(12) United States Patent
Okano et al.

(10) Patent No.: US 10,980,909 B2
(45) Date of Patent: Apr. 20, 2021

(54) ION GENERATING DEVICE AND METHOD FOR MANUFACTURING ION GENERATING DEVICE

(71) Applicant: SHARP KABUSHIKI KAISHA, Sakai (JP)

(72) Inventors: Satoshi Okano, Sakai (JP); Tetsuya Ezaki, Sakai (JP); Takahiro Matsuyama, Sakai (JP); Nobuyuki Ohe, Sakai (JP); Mitsuyoshi Yamashita, Sakai (JP); Minako Taniguchi, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 392 days.

(21) Appl. No.: 15/753,672

(22) PCT Filed: Oct. 13, 2016

(86) PCT No.: PCT/JP2016/080372
§ 371 (c)(1),
(2) Date: Feb. 20, 2018

(87) PCT Pub. No.: WO2017/168800
PCT Pub. Date: Oct. 5, 2017

(65) Prior Publication Data
US 2018/0243462 A1 Aug. 30, 2018

(30) Foreign Application Priority Data
Mar. 28, 2016 (JP) .............................. JP2016-064694

(51) Int. Cl.
*H01T 19/04* (2006.01)
*H01T 23/00* (2006.01)
(Continued)

(52) U.S. Cl.
CPC .............. *A61L 9/22* (2013.01); *B60H 3/0071* (2013.01); *F24F 7/00* (2013.01); *F24F 8/192* (2021.01);
(Continued)

(58) Field of Classification Search
CPC .... A61L 9/22; A61L 2209/15; A61L 2209/11; F24F 3/166; F24F 7/00; F24F 2003/1682; B60H 3/0071; H01T 23/00; H01T 19/04
(Continued)

(56) References Cited

U.S. PATENT DOCUMENTS 4,734,580 A * 3/1988 Rodrigo .................. H01T 23/00
250/324
5,245,386 A * 9/1993 Asano ................ G03G 15/0216
361/225
(Continued)

FOREIGN PATENT DOCUMENTS

CN 1155008 C 6/2004
JP H08-112549 A 5/1996
(Continued)

*Primary Examiner* — Dharti H Patel
(74) *Attorney, Agent, or Firm* — ScienBiziP, P.C.

(57) ABSTRACT

An ion generating device (1) includes discharge electrodes (21·22) each having a plurality of electrically conductive members (25·26) which form respective tip surfaces (36·37). A longer dimension direction of the tip surfaces (36·37) is nonparallel to an air sending direction (A). This allows for efficient release of ions.

10 Claims, 16 Drawing Sheets

(51) Int. Cl.
 *A61L 9/22* (2006.01)
 *F24F 8/192* (2021.01)
 *F24F 7/00* (2021.01)
 *B60H 3/00* (2006.01)
 *F24F 8/30* (2021.01)

(52) U.S. Cl.
 CPC ............ *H01T 19/04* (2013.01); *H01T 23/00* (2013.01); *A61L 2209/11* (2013.01); *A61L 2209/15* (2013.01); *F24F 8/30* (2021.01)

(58) Field of Classification Search
 USPC ........................................................ 361/231
 See application file for complete search history.

(56) References Cited

U.S. PATENT DOCUMENTS

| | | | | |
|---|---|---|---|---|
| 5,486,907 | A | * | 1/1996 | Watanabe .......... G03G 15/0216 361/225 |
| 9,948,071 | B2 | * | 4/2018 | Chen ........................ H01T 23/00 |
| 2009/0042502 | A1 | * | 2/2009 | Kim ...................... B60H 3/0071 454/139 |
| 2010/0175391 | A1 | * | 7/2010 | Jee ........................ B60H 3/0071 62/3.1 |
| 2013/0120895 | A1 | | 5/2013 | Lai |
| 2016/0204581 | A1 | * | 7/2016 | Nishida ................... H01T 19/04 250/423 F |
| 2016/0228882 | A1 | * | 8/2016 | Lin ........................... B03C 3/66 |

FOREIGN PATENT DOCUMENTS

| | | |
|---|---|---|
| JP | 2004-136783 A | 5/2004 |
| JP | 2004-342528 A | 12/2004 |
| JP | 4099215 B1 | 6/2008 |
| JP | 3174998 U | 4/2012 |
| TW | M432712 U | 7/2012 |
| WO | 2015-049920 A1 | 4/2015 |
| WO | 2015/151309 A1 | 10/2015 |

* cited by examiner (a)

(b)

ION GENERATING DEVICE AND METHOD FOR MANUFACTURING ION GENERATING DEVICE

TECHNICAL FIELD

The present invention relates to an ion generating device and a method for manufacturing the ion generating device.

BACKGROUND ART

An ion generating device has been conventionally used for, for example, indoor air cleaning, sterilization, or deodorization.

An ion generating device generally includes a discharge electrode for generating ions by electric discharge. An ion generating device generates ions by, for example, causing corona discharge to occur between (a) a tip of a discharge electrode to which a high voltage is applied and (b) an induction electrode.

As a discharge electrode for generating ions by thus applying thereto a high voltage, a brush-like discharge electrode including a plurality of fibrous electrically conductive members having bundled roots is known.

Patent Literature 1 discloses a discharge electrode used in a spark plug. A central electrode of Patent Literature is a brush-like discharge electrode constituted by a plurality of extremely thin carbon fibers bound together. A ground electrode is provided opposite to the central electrode such that there is a gap between the ground electrode and a head surface of the central electrode. Release of electrons from the central electrode toward the ground electrode generates a spark between the central electrode and the ground electrode. This ignites an air-fuel mixture supplied into an engine cylinder.

Furthermore, Patent Literature 1 discloses the tip surface of the central electrode having a mortar shape such that a central portion of the tip surface is depressed (that is, such that edge portions of the tip surface are protruding), or, conversely, a mountain shape such that the central portion of the tip surface is protruding. With these shapes, protruding parts of the tip surface are closer to the ground electrode than other parts. Patent Literature 1 discloses that with this configuration, electrons are more readily released from the protruding portions.

Note that dirt or dust adhering to a discharge surface of an ion generating device causes a decrease in an amount of ions generated. As such, in order to prevent such a decrease, it is necessary to periodically clean the discharge surface.

Patent Literature 2 discloses a technique for cleaning a discharge surface of an ion generating device. In Patent Literature 2, a sealing lip is mounted to a shut valve which is rotatably provided in an air conditioning duct. The sealing lip contacts and cleans the discharge surface when the shut valve rotates.

CITATION LIST

Patent Literature

[Patent Literature 1]
Japanese Patent No. 4099215
[Patent Literature 2]
Japanese Patent Application Publication, Tokukai, No. 2004-136783

SUMMARY OF INVENTION

Technical Problem

In a case where the brush-like discharge electrode which generates ions through electric discharge has a head surface which is flat, more ions will be released from the edge portions of the head surface than from the central portion of the head surface. Because the central electrode of Patent Literature 1 has a head surface which is circular, the number of carbon fibers located in edge portions is small, and thus electrons are not released efficiently.

Furthermore, in an ion generating device, air is blown onto the brush-like discharge electrode from one direction. It is by this air being sent that ions discharged by the brush-like discharge electrode are released to outside the ion generating device. In a case where a discharge electrode has a head surface which is circular, the head surface will have a small surface area and will therefore receive only a small amount of air. This issue as well prevents ions from being efficiently released to outside the ion generating device.

Furthermore, in an ion generating device, air is blown onto the brush-like discharge electrode from one direction. It is by this air being sent that ions discharged by the brush-like discharge electrode are released to outside the ion generating device. In a case where a discharge electrode has a head surface which is circular, the head surface will have a small surface area and will therefore receive only a small amount of air. This issue as well prevents ions from being efficiently released to outside the ion generating device.

The present invention has been made in view of the above problems. An object of the present invention is to provide an ion generating device which can release ions efficiently.

Solution to Problem

In order to solve the above problems, an ion generating device in accordance with an aspect of the present invention is an ion generating device including: a discharge electrode for generating ions by electric discharge, the discharge electrode including (i) a tip part having a plurality of linear electrically conductive members, (ii) a binding part for binding together respective base end parts of the plurality of linear electrically conductive members, and (iii) a mounting part for mounting the binding part on the ion generating device, the plurality of linear electrically conductive members forming a tip surface which is shaped so as to have a longer dimension direction and a shorter dimension direction, an air sending direction, in which gas is sent to the discharge electrode in order to carry the ions, being non-parallel to the longer dimension direction of the tip surface.

Advantageous Effects of Invention

An aspect of the present invention brings about an effect of making it possible to release ions efficiently.

DESCRIPTION OF EMBODIMENTS

Embodiment 1

Embodiment 1 of the present invention is described below with reference to FIG. 1 through FIG. 7.

(Overall Configuration of Ion Generating Device 1)

Figure 1:
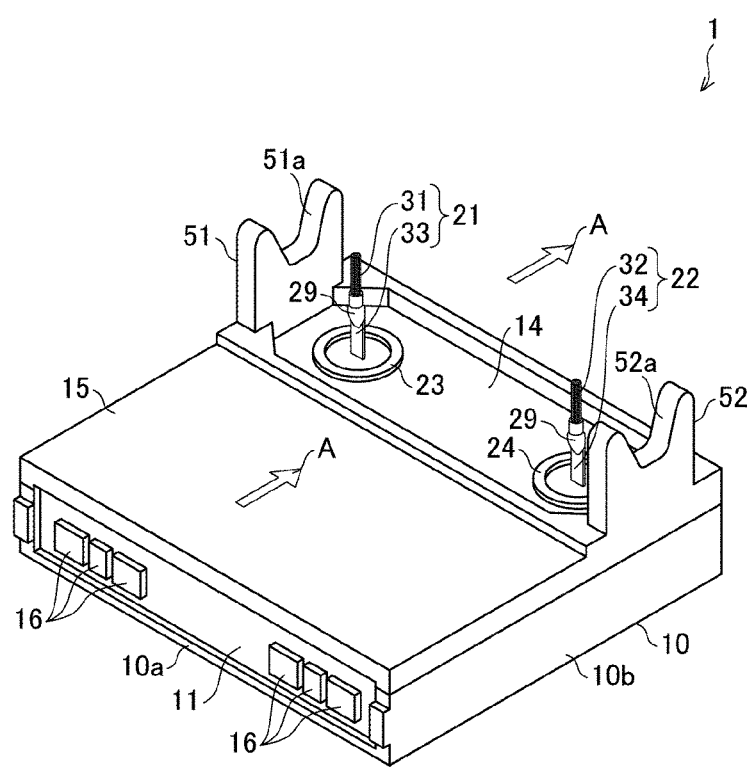
FIG. 1 is a perspective view schematically illustrating a configuration of an ion generating device in accordance with Embodiment 1 of the present invention.
Figure 2:
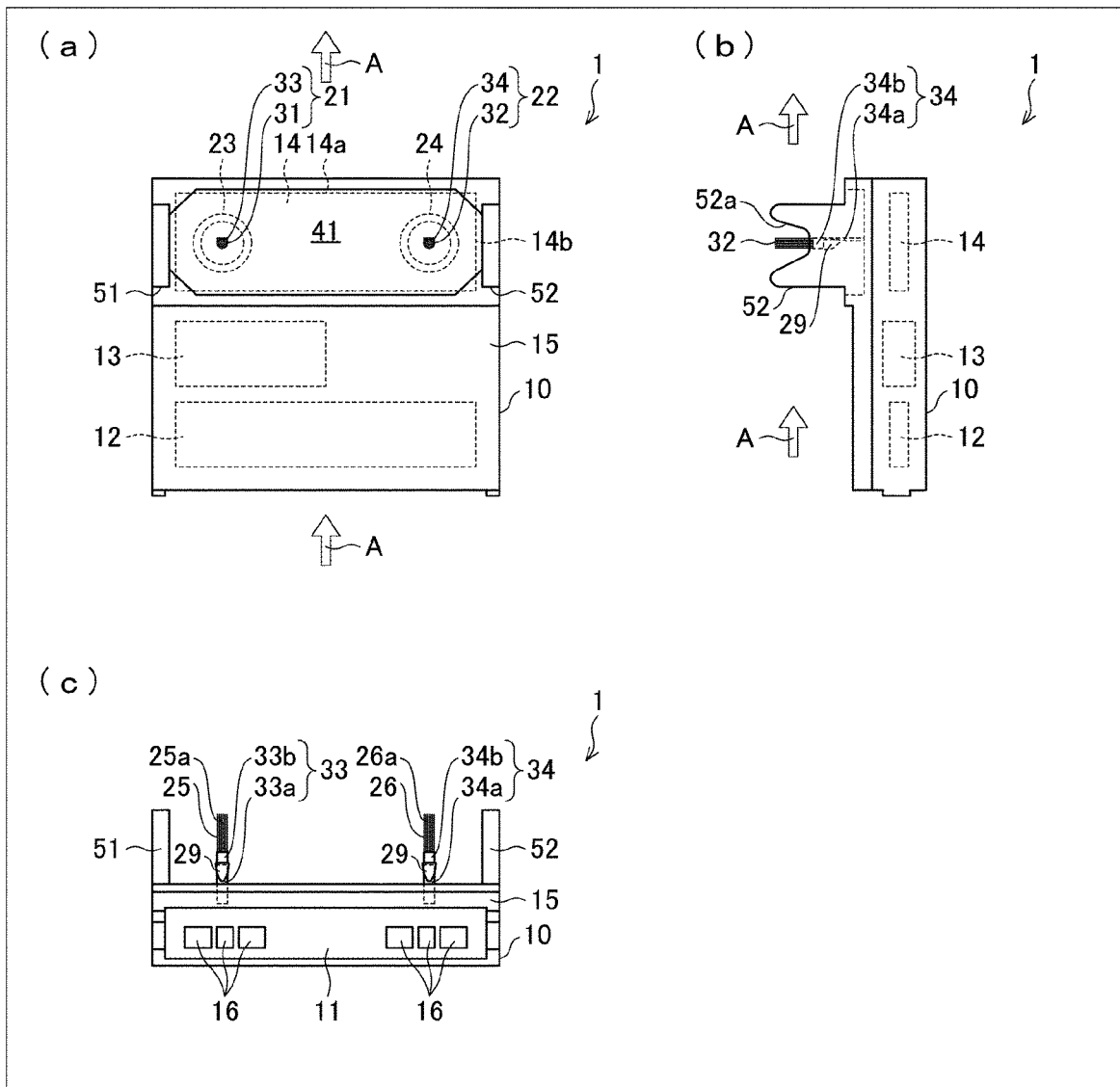
FIG. 2 is a diagram schematically illustrating the ion generating device.

First, a configuration of an ion generating device 1 is schematically described with reference to FIG. 1 and FIG. 2. FIG. 1 is a perspective view schematically illustrating the configuration of the ion generating device 1. FIG. 2 consists of a front view, a plan view, and a side view each schematically illustrating the configuration of the ion generating device 1.

As illustrated in FIG. 1 and FIG. 2, an ion generating device 1 includes a case 10 (housing), which is quadrangular, a substrate 12 for a transformer drive circuit (hereinafter referred to as a "transformer drive circuit substrate 12"), a high voltage transformer 13 (high voltage circuit), a substrate 14 for an ion generating element (hereinafter referred to as an "ion generating element substrate 14"), a lid 15, discharge electrodes 21 and 22, and protective plates 51 and 52 (protruding members).

The case 10 is box-shaped, has a front surface and an upper surface, each of which is open, and is made of an insulating resin. The case 10 has a front part that is provided with a substrate 11 for external connection (hereinafter referred to as an "external connection substrate 11"). The case 10 contains therein the transformer drive circuit substrate 12, the high voltage transformer 13, and the ion generating element substrate 14, which are arranged in this order from the front side. The case 10 has an upper surface to which the lid 15 is provided so as to cover the external connection substrate 11, the transformer drive circuit substrate 12, and the high voltage transformer 13.

The external connection substrate 11 has a surface that is provided with a plurality of (e.g., six) connection terminals 16. Each of the plurality of connection terminals 16 is made of an electrically conductive film provided on the surface of the external connection substrate 11 and is formed by, for example, print patterning, plating, sputtering, or chemical vapor deposition (CVD). The electrically conductive film is made of a material such as copper (Cu), aluminum (Al), gold (Au), or an alloy of copper (Cu), aluminum (Al), and gold (Au), and has a thickness of an order of several ten µm (e.g., a thickness of 35 µm). The connection terminals 16 are provided so as to be exposed on an outside of the case 10 while the external connection substrate 11 is being supported by the case 10.

The transformer drive circuit substrate 12 is provided with a high voltage transformer drive circuit. The high voltage transformer drive circuit is directed to drive the high voltage transformer 13 by an externally inputted voltage.

The high voltage transformer 13 is directed to be driven by the high voltage transformer drive circuit so as to raise a voltage supplied thereto. The ion generating element substrate 14 is provided with an ion generating element. The ion generating element is directed to generate at least either of positive ions and negative ions in response to application thereto of the voltage raised by the high voltage transformer 13.

The ion generating element includes discharge electrodes 21 and 22 and induction electrodes 23 and 24, which are circular. The discharge electrode 21 is provided to one side part of the ion generating element substrate 14, and the induction electrode 23 is provided around a place where the discharge electrode 21 is provided. The discharge electrode 22 is provided to the other side part of the ion generating element substrate 14, and the induction electrode 24 is provided around a place where the discharge electrode 22 is provided.

The induction electrode 23 is an electrode for forming an electric field between the induction electrode 23 and the discharge electrode 21, and the induction electrode 24 is an electrode for forming an electric field between the induction electrode 24 and the discharge electrode 22. The discharge electrode 21 is an electrode for generating negative ions between the discharge electrode 21 and the induction electrode 23, whereas the discharge electrode 22 is an electrode for generating positive ions between the discharge electrode 22 and the induction electrode 24. Note that the induction electrodes 23 and 24 each have ground electric potential.

As illustrated in FIG. 2, the ion generating element substrate 14 has a surface that is covered with an insulating sealing member 41 (resin). The insulating sealing member 41 can be an insulating material such as a heat-curable epoxy resin. The insulating sealing member 41 can be formed by heating a resin material and causing the resin material to cure.

With the insulating sealing member 41, base end parts of mounting parts 33a and 34a of the discharge electrodes 21 and 22 are sealed. Note that as described later, the mounting parts 33a and 34a are members for mounting a plurality of linear electrically conductive members 25 and 26 of the discharge electrodes 21 and 22, respectively, on the ion generating device 1 (more specifically, the ion generating element substrate 14). In a case where the insulating sealing member 41 is provided, the mounting parts 33a and 34a can be provided with insulation protection against a high voltage.

The ion generating element substrate 14 has a surface that is covered with an insulating sealing member 41 whose surface, for example, substantially does not differ in level from a surface of the lid 15. The discharge electrodes 21 and 22, which are provided so as to perpendicularly extend from the surface of the ion generating element substrate 14, protrude from the surface of the insulating sealing member 41.

The discharge electrode 21 is a brush-like discharge electrode including (i) a tip part 31 which has a plurality of linear electrically conductive members 25 and is formed like a brush and (ii) a base end part 33 to which the plurality of linear electrically conductive members 25 is attached. The discharge electrode 22 is a brush-like discharge electrode including (i) a tip part 32 which has a plurality of linear electrically conductive members 26 and is formed like a brush and (ii) a base end part 34 to which the plurality of electrically conductive members 26 is attached.

Note that the tip parts 31 and 32 refer to parts located ahead of the respective base end parts 33 and 34. Specifically, the tip part 31 refers to a part that extends from a tip surface (head surface) 36 formed by ends of the plurality of electrically conductive members 25, which are in a brush-like bundle, to a connection end (contact end) of the plurality of electrically conductive members 25 at which connection end (contact end) the plurality of electrically conductive members 25 is in connection (in contact) with the base end part 33. The tip part 32 refers to a part that extends from a tip surface (head surface) 37 formed by ends of the plurality of electrically conductive members 26, which are in a brush-like bundle, to a connection end (contact end) of the plurality of electrically conductive members 26 at which connection end (contact end) the plurality of electrically conductive members 26 is in connection (in contact) with the base end part 34. Note also that the term "linear" encompasses terms such as "thread-like", "fibrous", and "wire-like".

The tip parts 31 and 32 of the discharge electrodes 21 and 22 are made of an electrically conductive member such as metal, carbon fiber, electrically conductive fiber, or electrically conductive resin. The plurality of electrically conductive members 25 of the tip part 31 and the plurality of electrically conductive members 26 of the tip part 32 each have an outside diameter of not less than 5 μm and not more than 30 μm. In a case where each of the plurality of electrically conductive members 25 and each of the plurality of electrically conductive members 26 has an outside diameter of not less than 5 μm, the plurality of electrically conductive members 25 and the plurality of electrically conductive members 26 can be mechanically strong and also can be prevented from being electrically worn. Meanwhile, in a case where each of the plurality of electrically conductive members 25 and each of the plurality of electrically conductive members 26 has an outside diameter of not more than 30 μm, the plurality of electrically conductive members 25 and the plurality of electrically conductive members 26 can bend like hair, so that the plurality of electrically conductive members 25 and the plurality of electrically conductive members 26 easily spread and easily sway.

Each of the plurality of electrically conductive members 25 and each of the plurality of electrically conductive members 26 can be a carbon fiber having an outside diameter of 7 μm, or an electrically conductive fiber made of stainless steel (SUS) and having an outside diameter of 12 μm or 25 μm.

The base end part 33 of the discharge electrode 21 has (i) the mounting part 33a, which is sheet metal, for mounting the discharge electrode 21 on the ion generating element substrate 14 and (ii) a binding part 33b for binding the plurality of electrically conductive members 25 of the tip part 31 at the connection end. As in the case of base end part 33 of the discharge electrode 21, the base end part 34 of the discharge electrode 22 has (i) the mounting part 34a, which is sheet metal, for mounting the discharge electrode 22 on the ion generating element substrate 14 and (ii) a binding part 34b for binding the plurality of electrically conductive members 26 of the tip part 32 at the connection end.

Next, the protective plates 51 and 52 are described. The ion generating device 1 is not necessarily placed, during a period in which the ion generating device 1 has been produced and then is mounted in various electrical apparatuses, on a base on which to place the ion generating device 1 (hereinafter, the "base" is referred to as a "placing base", not illustrated) in such a state as illustrated in each of FIG. 1 and FIG. 2. For example, the ion generating device 1 which is placed on the placing base in such a state as illustrated in each of FIG. 1 and FIG. 1 may be turned upside down so as to be placed on the placing base.

In this way, overturning of the ion generating device 1 during, for example, a production process may cause breakage (deformation) such as a break in a brush part which break is caused by a contact between (a) the discharge electrodes 21 and 22 and (b) a floor such as the placing base.

In order to overcome the above problem, Embodiment 1 is arranged such that the protective plates 51 and 52 for protecting the respective discharge electrodes 21 and 22 protrude so as to be adjacent to the respective discharge electrodes 21 and 22. Note that according to Embodiment 1, the ion generating element substrate 14 in which the discharge electrodes 21 and 22 protrude is provided in an end of a rear part of the upper surface of the case 10, which is quadrangular.

The ion generating element substrate 14 is rectangular, and the discharge electrodes 21 and 22 are arranged in a longer side direction of the ion generating element substrate 14. The ion generating element substrate 14 has a long side 14a that (i) is a side parallel to the direction in which the discharge electrodes 21 and 22 are arranged and (ii) faces a side 10a of the rear part of the case 10 so as to be parallel to the side 10a.

In view of the above, according to Embodiment 1, on both ends of the rear part of the upper surface of the case 10, the protective plates 51 and 52 protrude so as to be adjacent to the respective discharge electrodes 21 and 22.

The protective plates 51 and 52 are juxtaposed to each other while the discharge electrodes 21 and 22 are sandwiched therebetween in the longer side direction of the ion generating element substrate 14 (i.e., a direction parallel to the long side 14a of the ion generating element substrate 14), which longer side direction is the direction in which the discharge electrodes 21 and 22 are arranged.

The protective plates 51 and 52 have a height whose maximum value is greater than a height of the discharge electrodes 21 and 22. The protective plates 51 and 52 vertically protrude, on the insulating sealing member 41 or in an upper part of the lid 15, or by being integrally molded with the lid 15, so as to further protrude from the surface of the ion generating element substrate 14 than the tip parts 31 and 32 of the discharge electrodes 21 and 22.

With the arrangement, even in a case where the ion generating device 1 is, for example, overturned, the discharge electrodes 21 and 22 can be prevented from directly contacting an object, provided on an outside of the ion generating device 1, such as the placing base, so that the discharge electrodes 21 and 22 can be prevented from, for example, being broken by the contact.

Note here that the height of the protective plates 51 and 52 refers to a vertical length, i.e., a height from the surface of the insulating sealing member 41 to an upper surface of the protective plate 51 as well as a height from the surface of the insulating sealing member 41 to an upper surface of the protective plate 52.

The height of the protective plates 51 and 52 is not particularly limited provided that the protective plates 51 and 52 further protrude from the surface of the ion generating element substrate 14 than the tip parts 31 and 32 of the discharge electrodes 21 and 22.

Note, however, that the protective plates 51 and 52 which have a greater height make the ion generating device 1 larger in size accordingly. Thus, the protective plates 51 and 52 desirably have a height that is great enough for the discharge electrodes 21 and 22 to be prevented from directly contacting the object, provided on the outside of the ion generating device 1, such as the placing base in a case where the ion generating device 1 is, for example, overturned.

For example, the height from the surface of the insulating sealing member 41 to the upper surfaces of the protective plates 51 and 52 is desirably slightly greater than a height from the surface of the insulating sealing member 41 to tips of the tip parts 31 and 32 (i.e., a maximum value of a height from the surface of the insulating sealing member 41 to the tips 36 and 37 of the electrically conductive members 25 and the electrically conductive members 26) in the discharge electrodes 21 and 22.

The protective plates 51 and 52 are spaced from the respective discharge electrodes 21 and 22 so that a distance between the discharge electrode 21 and the protective plate 51 and a distance between the discharge electrode 22 and the protective plate 52 are each longer than the length of the tip parts 31 and 32 of the discharge electrodes 21 and 22.

Thus, even in a case where the electrically conductive members 25 or the electrically conductive members 26 repel each other and the tip part 31 or 32 spreads, so that the electrically conductive members 25 or the electrically conductive members 26 lean at any angle, the electrically conductive members 25 and the electrically conductive members 26 do not directly contact the respective protective plates 51 and 52. This makes it possible to prevent occurrence of a leakage.

When the discharge electrodes 21 and 22 are seen through the respective protective plates 51 and 52 (i.e., when the ion generating device 1 is seen from a direction parallel to the side 10a of the case 10), respective parts of the protective plates 51 and 52 which parts face the respective tip parts 31 and 32 of the discharge electrodes 21 and 22 are each formed in a shape of a notched plate. Thus, the protective plate 51 is provided with an opening 51a, facing the discharge electrode 21, for exposing the tip part 31. Meanwhile, the protective plate 52 is provided with an opening 52a, facing the discharge electrode 22, for exposing the tip part 32.

The protective plates 51 and 52, which are thus provided with the respective openings 51a and 52a, do not inhibit the discharge electrodes 21 and 22 from releasing ions, so that the ions can be satisfactorily released.

As illustrated in FIGS. 1 and 2, a gas, such as air, which carries ions released from the discharge electrodes 21 and 22 is sent in a front-to-rear direction of the ion generating device 1. Note that, herein, a direction in which the ion-carrying gas is sent is referred to as an air sending direction A. The air sending direction A is indicated by an arrow in FIG. 1 etc.

(Discharge Electrode)

Figure 3:
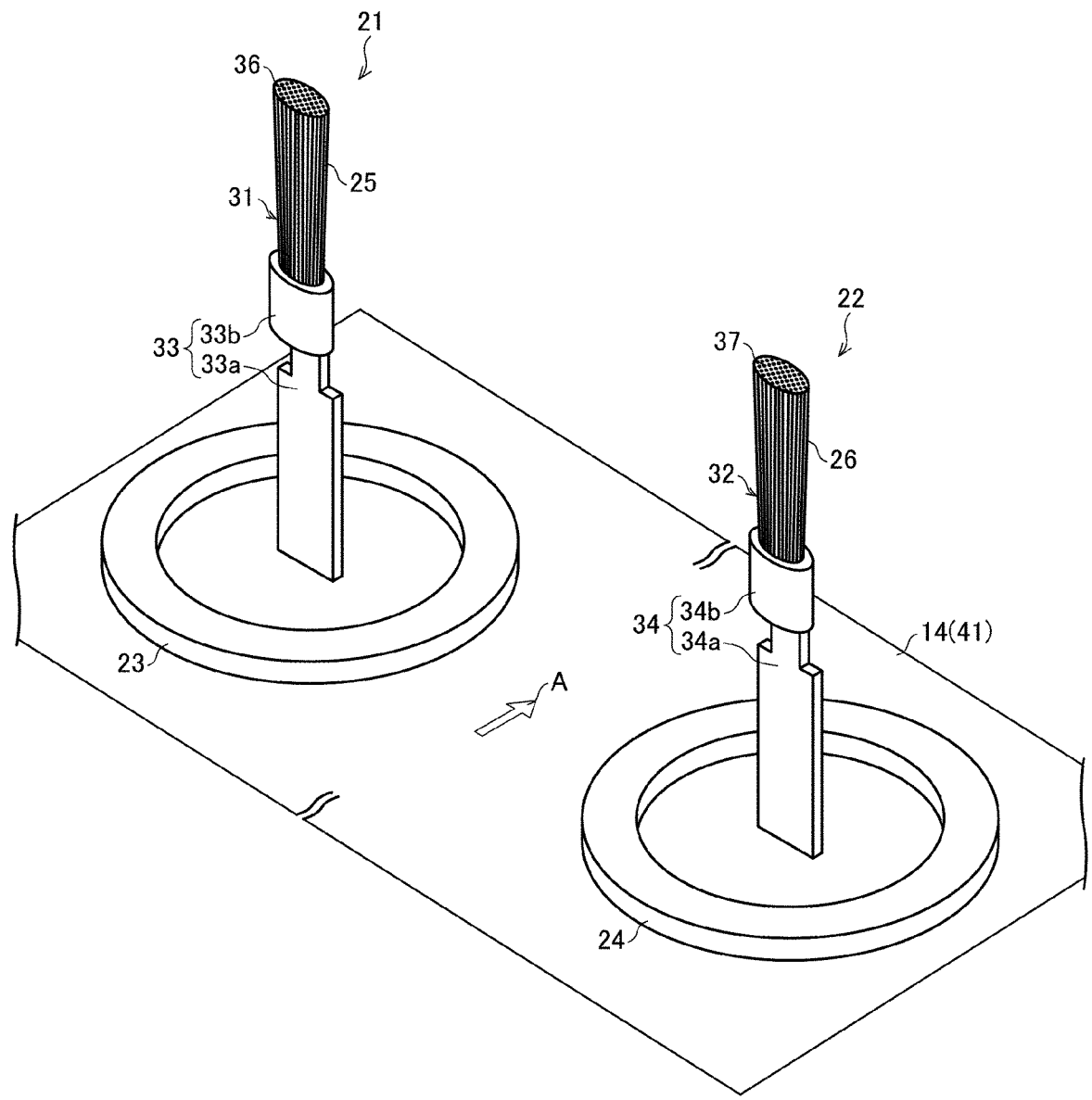
FIG. 3 is a perspective view illustrating a configuration of (i) discharge electrodes of the ion generating device and (ii) a vicinity of the discharge electrodes.
Figure 4:
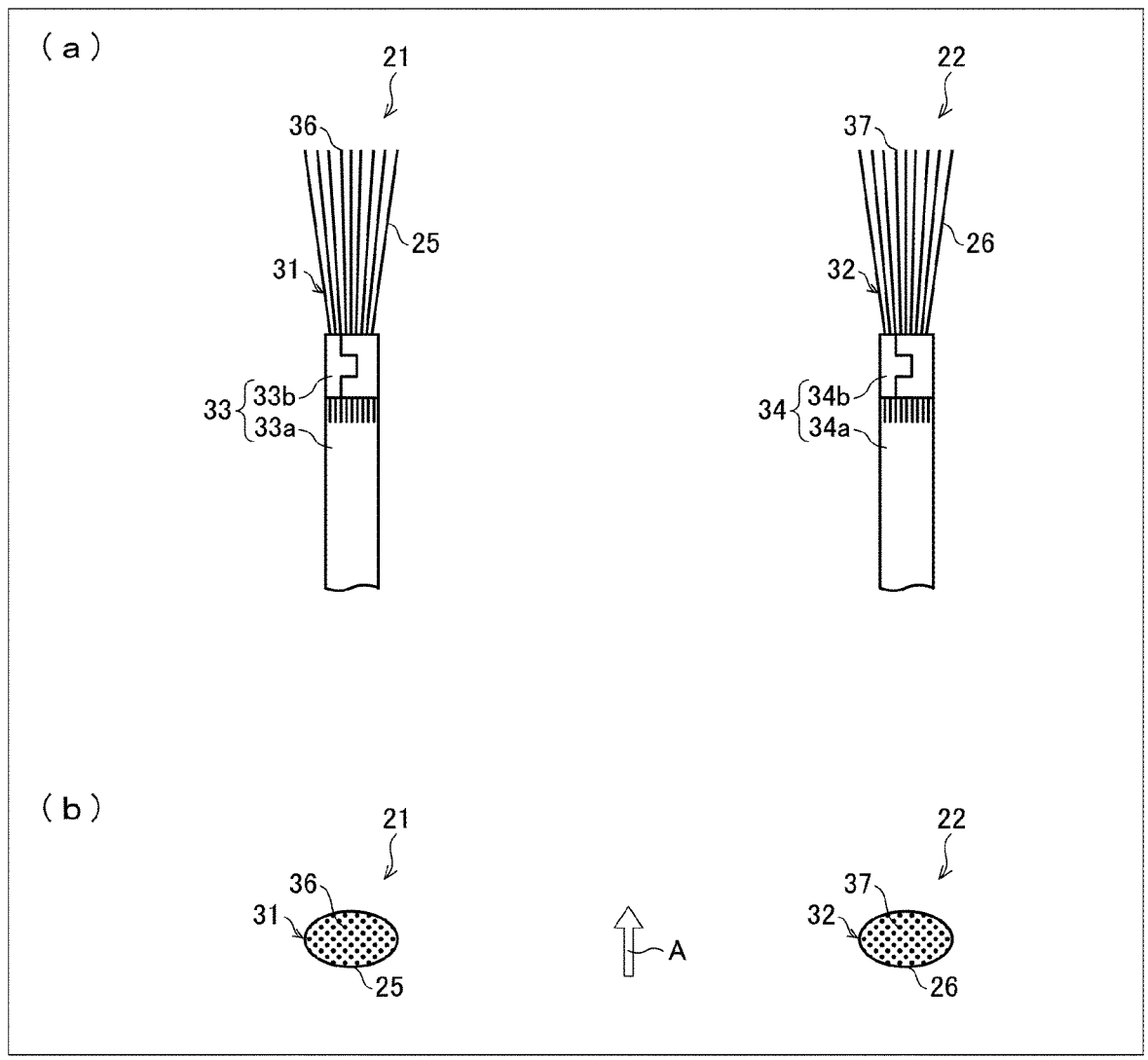
FIG. 4 is a diagram illustrating a configuration of the discharge electrodes.
Figure 5:
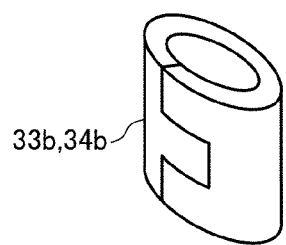
FIG. 5 is a perspective view illustrating a configuration of a binding part of the discharge electrodes.

Next, a configuration of (i) discharge electrodes of Embodiment 1 and (ii) a vicinity thereof is more specifically described with reference to FIGS. 3 to 7. FIG. 3 is a perspective view which illustrates a configuration of the discharge electrodes and their vicinity. FIG. 4 illustrates the configuration of the discharge electrodes. (a) of FIG. 4 is an elevational view illustrating the configuration of the discharge electrodes, and (b) of FIG. 4 is a top view illustrating the configuration of the discharge electrodes. FIG. 5 is a perspective view illustrating a configuration of the binding part 33b and the binding part 34b.

As described above, a direction along which the discharge electrodes 21 and 22 are arranged is perpendicular to the air sending direction A.

The binding parts 33b and 34b each hold a base end part of a respective brush (may also be referred to as a "brush part") so as to bind (caulk) the base end part, each brush including a respective one of plurality of linear electrically conductive members 25 and 26. The mounting parts 33a and 34a each have a base end part that is sealed with the insulating sealing member 41.

As illustrated in FIGS. 4 and 5, the binding parts 33b and 34b each have an elliptical opening into which the plurality of electrically conductive members 25 and 26, respectively, are inserted. Due to the elliptical opening, the plurality of electrically conductive members 25 and 26 being respectively bound by the binding parts 33b and 34b also take on an elliptical shape. This means that the respective tip surfaces 36 and 37 of the tip parts 31 and 32 also have an elliptical shape. With this configuration, in comparison to a configuration in which the tip surfaces are circular in shape, there is a greater number of the electrically conductive members 25 and 26 which are positioned in peripheral portions. There is also an increase in surface areas of respective edge portions of the tip surfaces 36 and 37, which edge portions release ions more readily than central portions. As such, the ion generating device 1 including the discharge electrodes 21 and 22 makes it possible to release ions more efficiently. A configuration which satisfies $L1/L2 \geq 1.5$ is preferable, where L1 is a dimension of the respective tip surfaces 36 and 37 along a longer dimension direction thereof, and L2 is a dimension of the respective tip surfaces 36 and 37 along a shorter dimension direction thereof, the shorter dimension direction being orthogonal to the longer dimension direction. A configuration which satisfies $L1/L2 \geq 2$ is even more preferable, since the number of electrically conductive members 25 and 26 which are positioned in peripheral portions will be further increased.

The tip surfaces 36 and 37 of the tip parts 31 and 32 are flat and are substantially parallel to the surface of the ion generating element substrate 14 on which the discharge electrodes 21 and 22 are provided.

After the plurality of electrically conductive members 25 and 26 are bound by the respective binding parts 33b and 34b, the tip parts 31 and 32 are created by a cutting step in which the plurality of electrically conductive members 25 and 26 are cut at the tip surfaces 36 and 37 so as to have an optimal length. This makes it possible to create the tip parts 31 and 32 efficiently by a cutting step in which the tip surfaces 36 and 37 of the tip parts 31 and 32 are cut so as to be (i) flat and (ii) substantially parallel to the surface of the ion generating element substrate 14 on which the discharge electrodes 21 and 22 are provided.

The longer dimension direction of the elliptical shape of the tip surfaces 36 and 37 can be parallel to the air sending direction A of the ion generating device 1 but is preferably nonparallel to the air sending direction A. In comparison to a configuration where these directions are parallel, a configuration where these directions are nonparallel allows the tip surfaces 36 and 37, formed by the plurality of electrically conductive members 25 and 26 aligned along the longer dimension direction, to receive airflow more efficiently and therefore allows the discharge electrodes 21 and 22 to more efficiently release and spread ions from the tip surfaces 36 and 37.

Furthermore, the longer dimension direction of the elliptical shape of the tip surfaces 36 and 37 is more preferably perpendicular to the air sending direction A of the ion generating device 1. This allows the tip surfaces 36 and 37 to receive airflow even more efficiently and therefore allows the discharge electrodes 21 and 22 to even more efficiently release and spread ions from the tip surfaces 36 and 37.

The direction along which the discharge electrodes 21 and 22 are arranged is also preferably perpendicular to the air sending direction A. Such a configuration causes more air to be sent, in the air sending direction A. between the discharge electrodes 21 and 22 and allows the tip surfaces 36 and 37 to receive airflow more efficiently. The discharge electrodes 21 and 22 can therefore release and spread ions from the tip surfaces 36 and 37 even more efficiently. Note that a configuration may be employed in which the direction along which the discharge electrodes 21 and 22 are arranged and the air sending direction A are not perpendicular.

Note that the shape of the tip surfaces 36 and 37 of the tip parts 31 and 32 is not limited to an elliptical shape. The shape of the tip surfaces 36 and 37 need only have a longer dimension direction and a shorter dimension direction which is orthogonal to the longer dimension direction, and thus can be a variety of shapes. The shape of the tip surfaces 36 and 37 corresponds to the shape of respective openings of the binding parts 33b and 34b into which the plurality of electrically conductive members 25 and 26 are inserted. Therefore, by configuring the shape of the respective openings of the binding parts 33b and 34b so as to have a longer dimension direction and a shorter dimension direction which is orthogonal to the longer dimension direction, it is possible to cause the tip surfaces 36 and 37 to have a shape having a longer dimension direction and a shorter dimension direction which is orthogonal to the longer dimension direction as described above.

Figure 6:
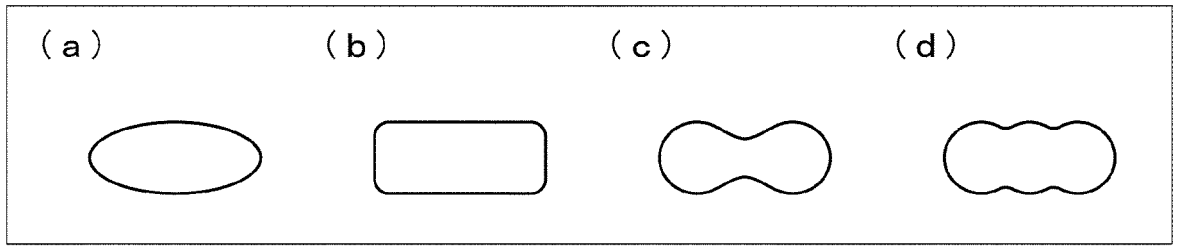
FIG. 6 is a diagram illustrating shapes of an opening of the binding part.

FIG. 6 illustrates shapes of the respective openings of the binding parts 33b and 34b into which the plurality of electrically conductive members 25 and 26 are inserted. (a) to (d) of FIG. 6 illustrate the binding parts 33b and 34b as viewed from above. As illustrated in (a) to (d) of FIG. 6, the respective openings of the binding parts 33b and 34b may take on a variety of shapes, provided that the shape has a longer dimension direction and a shorter dimension direction which is orthogonal to the longer dimension direction. Examples of possible shapes include (a) an elliptical shape, (b) a rectangular shape, (c) a shape in which two circles are connected, (d) a shape in which three circles are connected. Note that, as described above, configuring the respective openings of the binding parts 33b and 34b so as to have one of the shapes illustrated in (a) to (d) of FIG. 6 causes the tip surfaces 36 and 37 of the tip parts 31 and 32 to have a corresponding one of the shapes illustrated in (a) to (d) of FIG. 6.

Figure 7:
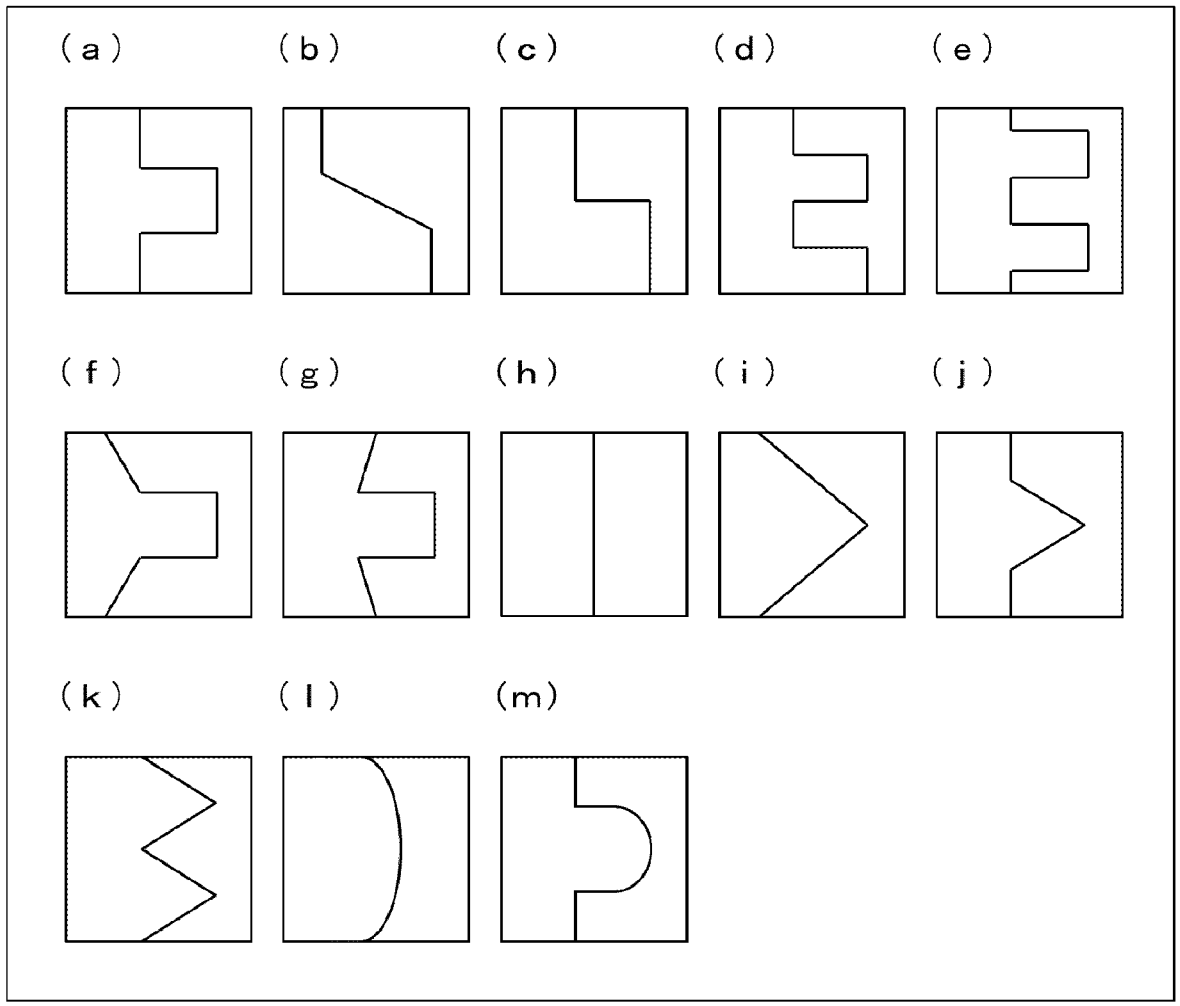
FIG. 7 is a diagram illustrating examples of caulking shapes in the binding part.

FIG. 7 illustrates examples of caulking shapes in the binding parts 33b and 34b. FIG. 7 illustrates the binding parts 33b and 34b as seen from the front. As illustrated in (a) to (m) of FIG. 7, the binding parts 33b and 34b are not limited to a particular caulking shape. A variety of caulking shapes can be employed.

(Method for Manufacturing Ion Generating Device 1)

Discussed next is a method of manufacturing the ion generating device 1.

First, a plurality of electrically conductive members is inserted into each of the binding parts 33b and 34b of the base end parts 33 and 34 and then bound (binding step). Then, the respective pluralities of electrically conductive members bound by the binding parts 33b and 34b are cut so as to have an optimal length (cutting step). This forms the tip parts 31 and 32. Thereafter, the respective base end parts 33 and 34 of the discharge electrodes 21 and 22, which have been provided with the tip parts 31 and 32, are mounted to the ion generating element substrate 14 (discharge electrode mounting step).

Next, the transformer drive circuit substrate 12, the high voltage transformer 13, and the ion generating element substrate 14 are disposed inside the case 10 (disposing step). Thereafter, the lid 15 and the protective plates 51 and 52 are assembled to the case 10 so as to cover the transformer drive circuit substrate 12 and the high voltage transformer 13. At this time, the discharge electrodes 21 and 22 protrude from an opening in the lid 15. In other words, the base end parts 33 and 34 of the discharge electrodes 21 and 22 are partially contained by the opening (containing section) of the lid 15

Next, an insulating resin material is filled into the opening of the lid 15 (filling step). The insulating resin material thus filled is cured by heating or the like so as to form the insulating sealing member 41. Forming the insulating sealing member 41 on the surface of the ion generating element substrate 14 in this manner seals a vicinity of portions of the discharge electrodes 21 and 22, in which portions the base end parts 33 and 34 are in contact with the ion generating element substrate 14 (sealing step). Note that possible examples of the resin material for filling include insulating materials such as epoxy resin and urethane resin.

Embodiment 2

Figure 8:
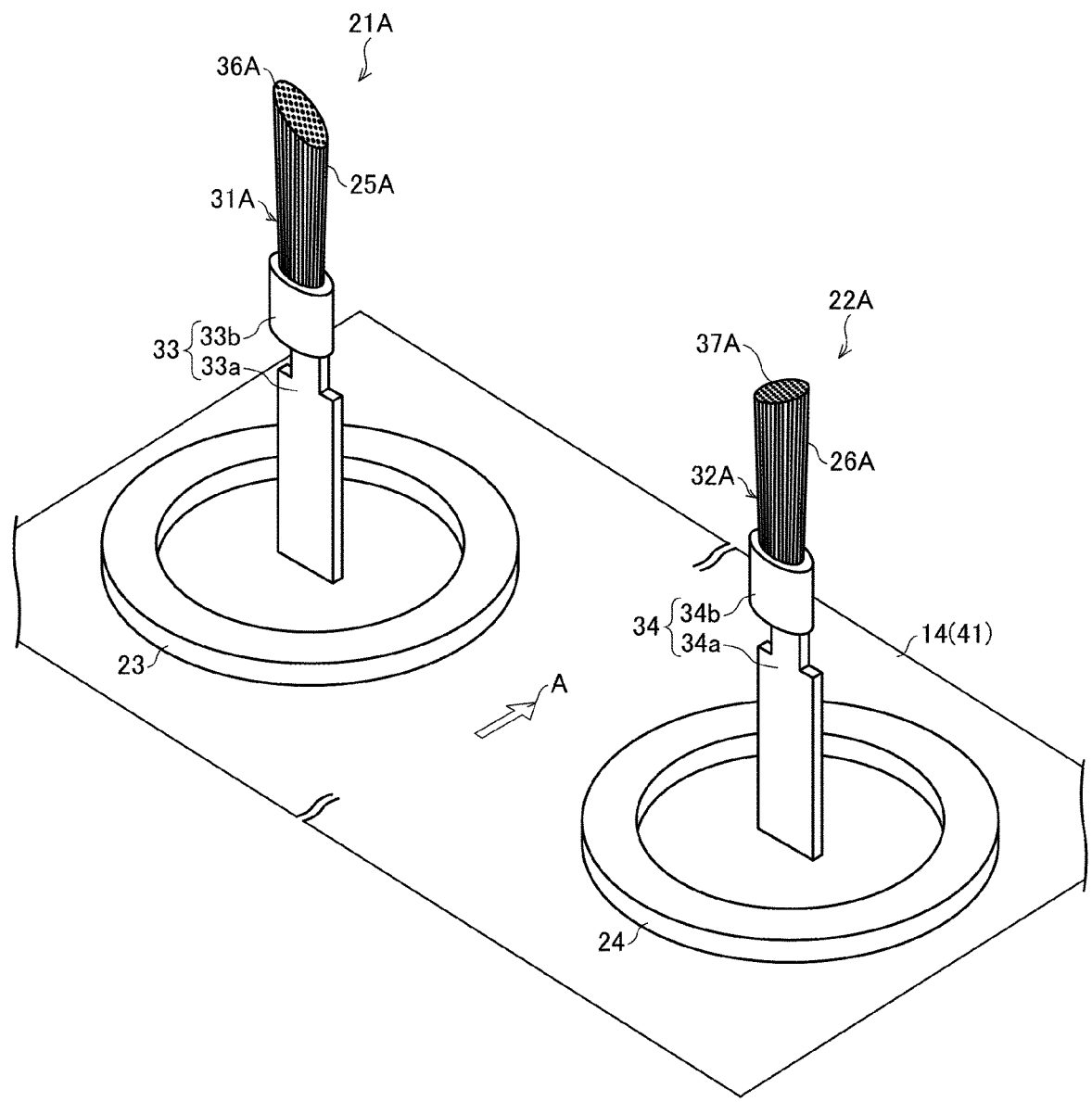
FIG. 8 is a perspective view illustrating a configuration of (i) discharge electrodes of an ion generating device in accordance with Embodiment 2 and (ii) a vicinity of the discharge electrodes.
Figure 9:
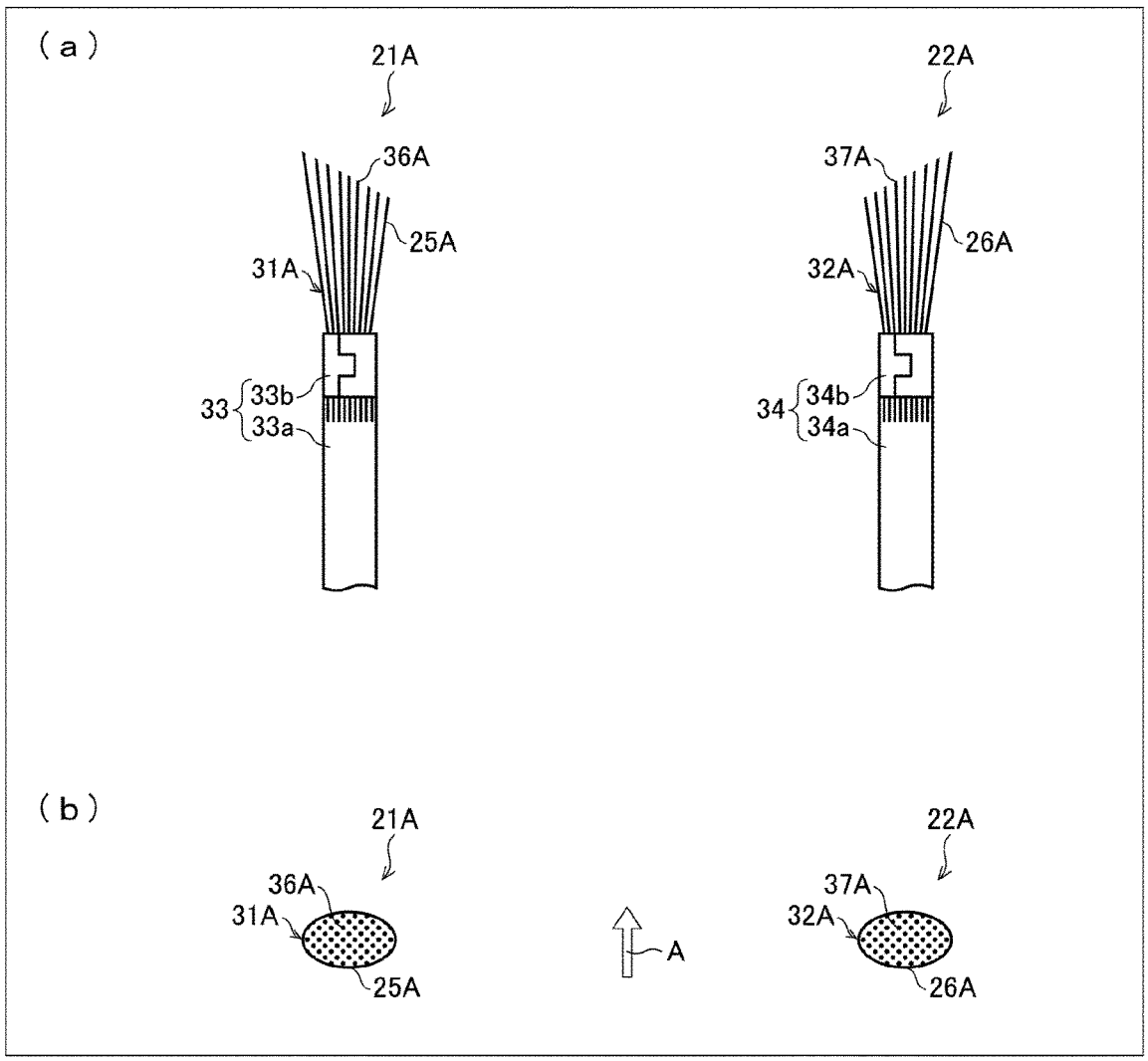
FIG. 9 is a diagram illustrating a configuration of the discharge electrodes.

The following description will discuss Embodiment 2 of the present invention with reference to FIGS. 8 and 9. For convenience, members similar in function to those described in Embodiment 1 will be given the same reference signs, and their description will be omitted.

FIG. 8 is a perspective view illustrating a configuration of (i) discharge electrodes of an ion generating device in accordance with Embodiment 2 and (ii) a vicinity of the discharge electrodes. FIG. 9 illustrates the configuration of the discharge electrodes. (a) of FIG. 9 is an elevational view illustrating the configuration of the discharge electrodes, and (b) of FIG. 9 is a top view illustrating the configuration of the discharge electrodes.

The ion generating device 1 may include, instead of discharge electrodes 21 and 22 (see FIG. 3 and FIG. 4), discharge electrodes 21A and 22A. Aside from the discharge electrodes 21A and 22A, the ion generating device 1 in accordance with Embodiment 2 is configurationally similar to the ion generating device 1 described in Embodiment 1.

The discharge electrode 21A includes a tip part 31A, instead of the tip part 31 included in the discharge electrode 21. The tip part 31A has a binding part 33b which binds, instead of the plurality of electrically conductive members 25 (see FIG. 3 and FIG. 4), a plurality of electrically conductive members 25A.

The discharge electrode 22A includes a tip part 32A, instead of the tip part 32 included in the discharge electrode 22. The tip part 32A has a binding part 34b which binds, instead of the plurality of electrically conductive members 26 (see FIG. 3 and FIG. 4), a plurality of electrically conductive members 26A.

The tip part 31A has a tip surface 36A which is inclined downwards (i.e., in a direction toward the ion generating element substrate 14) toward the discharge electrode 22A which is opposite the discharge electrode 21A. The tip part 32A has a tip surface 37A which is inclined downwards toward the discharge electrode 21A which is opposite the discharge electrode 22A.

Air is blown in the air sending direction A over the ion generating device 1 in order to cause ions released by the discharge electrodes 21A and 22A to be released to outside the ion generating device 1. This air is blown particularly intensively between the discharge electrodes 21A and 22A. As such, by configuring the tip surface 36A to be inclined downward toward the discharge electrode 22A which is arranged opposingly, and by configuring the tip surface 37A to be inclined downward toward the discharge electrode 21A which is arranged opposingly, it is possible for the tip surfaces 36A and 37A to efficiently receive air being sent in the air sending direction A. The discharge electrodes 21A and 22A can therefore release ions more efficiently.

Furthermore, a longer dimension direction of the tip surfaces 36A and 37A is parallel to the direction along which the discharge electrodes 21A and 22A are arranged. This allows the discharge electrodes 21A and 22A to release ions even more efficiently.

Furthermore, since the tip surfaces 36A and 37A are flat, it is possible to create the tip parts 31A and 32A efficiently by a cutting step.

Embodiment 3

The following description will discuss Embodiment 3 of the present invention with reference to FIGS. 10 to 13. For convenience, members similar in function to those described in Embodiments 1 and 2 will be given the same reference signs, and their description will be omitted.

Figure 10:
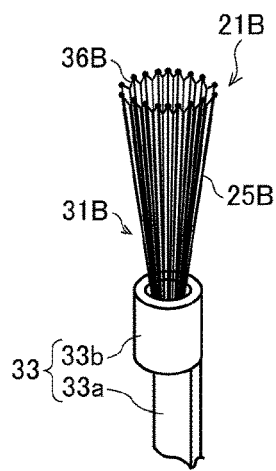
FIG. 10 is a perspective view illustrating a configuration of a discharge electrode of an ion generating device in accordance with Embodiment 3.
Figure 11:
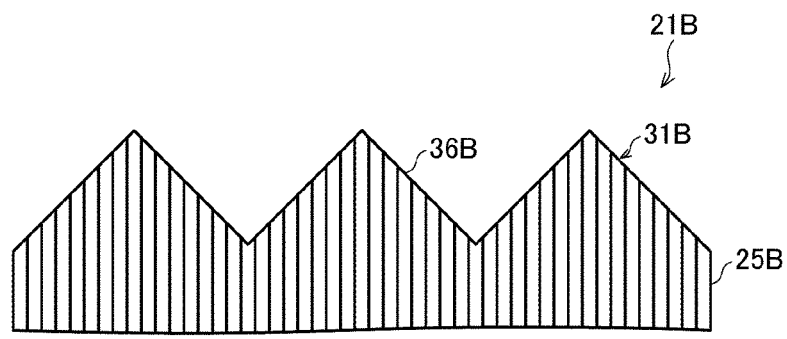
FIG. 11 is an elevational view illustrating a vicinity of a tip surface of a tip part of the discharge electrode.

FIG. 10 is a perspective view illustrating a configuration of a discharge electrode 21B of an ion generating device in accordance with Embodiment 3. FIG. 11 is an elevational view illustrating a vicinity of a tip surface of a tip part of the discharge electrode illustrated in FIG. 10.

The ion generating device 1 may include, instead of discharge electrodes 21 and 22 (see FIG. 3 and FIG. 4), discharge electrodes 21B and 21B. Aside from the discharge electrodes 21B and 21B, the ion generating device 1 in accordance with Embodiment 3 is configurationally similar to the ion generating device 1 described in Embodiment 1.

The discharge electrode 21B includes a tip part 31B, instead of the tip parts 31A and 32A included in the discharge electrodes 21A and 22A. The tip part 31B has a binding part 33b which binds, instead of the plurality of electrically conductive members 25 (see FIG. 3 and FIG. 4), a plurality of electrically conductive members 25B.

The tip part 31B has a tip surface 36B which is not flat, but rather has an uneven form having connected mountain-like shapes. The tip surface 36B is configured such that its edge portions have the uneven form, while its central portions are flat. Alternatively, the entirety of the tip surface 36B may have the uneven form.

As illustrated in FIG. 11, with the uneven form, tip surfaces of mutually adjacent ones of the plurality of electrically conductive members 25B form a continuous inclined surface. This makes it possible to easily create the uneven form when cutting the tip surface 36B in a cutting step.

Because the tip surface 36B of the tip part 31B of the discharge electrode 21B has the uneven form as described above, in comparison to a configuration in which the tip surface 36B is flat, there is an increase in surface area which receives air being sent in the air sending direction A. It is therefore possible to release ions efficiently.

Figure 12:
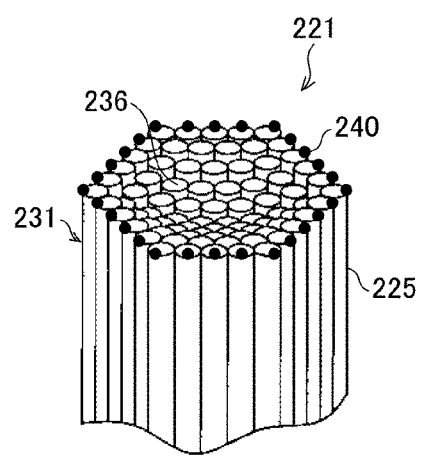
FIG. 12 is a perspective view illustrating a vicinity of a tip surface of a conventional central electrode.

FIG. 12 is a perspective view illustrating a vicinity of a tip surface of a central electrode disclosed in Patent Literature 1. As illustrated in FIG. 12, a tip part 231 of the central electrode 221 is constituted by a plurality of carbon fibers 225 which are bound. The tip surface 236 of the tip part 231 has a mortar shape with its center depressed. The tip surface 236 is also circular.

With a tip surface 236 which is (i) circular and (ii) flat or mortar-shaped, electric discharge readily occurs at edge portions thereof. As such, in a case where the tip part 231 is energized over a long period, adhered matter which is formed by the electric discharge is likely to adhere to the edge portions of the tip surface 236. In a case where this adhered matter is formed along the entire perimeter of edge portions of the tip surface 236, the plurality of carbon fibers 225 constituting the tip part 231 become a bunch and simulate a single, thick carbon fiber. In a case where the plurality of carbon fibers 225 simulate a single, thick carbon fiber in this manner, the efficiency of electron release by the tip surface 236 is decreased.

In contrast, in the discharge electrode 21B in accordance with Embodiment 3, the tip surface 36B of the tip part 31B has the uneven form. Therefore, electric discharge is particularly concentrated at protruding portions of the edge portions of the tip surface 36B. Due to this configuration, even in a case where adhered matter formed by electric discharge is formed on the tip surface 36B, the adhered matter is formed at a vertex of a protrusion and is unlikely to be formed between vertices of adjacent protrusions. Therefore, with the discharge electrode 21B, even in a case where the tip part 31B is energized over a long period, it is possible to maintain a state where the individual ones of the plurality of electrically conductive members 25B are separate from each other. As such, the discharge electrode 21B makes it possible to prevent a decrease in the efficiency of the release of ions. In other words, the discharge electrode 21B makes it possible to increase ion release efficiency in a case where ions are released over a long period.

Furthermore, in a case where the tip surface 36B has a shape having a longer dimension direction and a shorter dimension direction which is orthogonal to the longer dimension direction, such as an elliptical shape, it is possible to more efficiently increase ion release efficiency. Note that the tip surface 36B may also have, for example, a circular shape which does not have a longer dimension direction or a shorter dimension direction.

Figure 13:
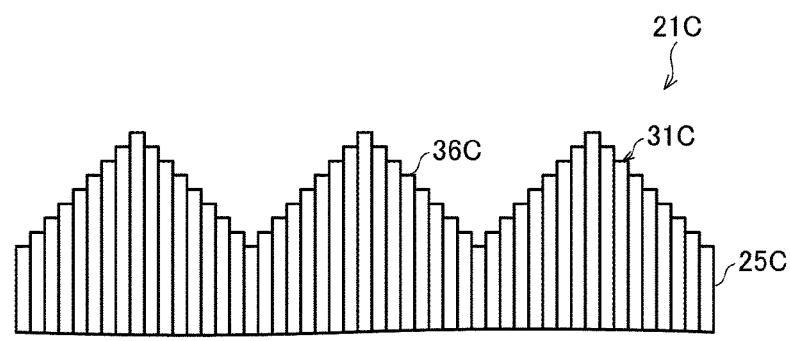
FIG. 13 is an elevational view illustrating a configuration of a tip surface of a tip part in a variation of the discharge electrode illustrated in FIG. 11.

FIG. 13 is an elevational view illustrating a configuration of a tip surface 36C of a tip part 31C of a discharge electrode 21C in accordance with a variation. As illustrated in FIG. 13, the discharge electrode 21C includes the tip part 31C which includes a plurality of electrically conductive members 25C which are bound. Tip surfaces of mutually adjacent ones of the plurality of electrically conductive members 25C are configured to be stepped such that the tip surface 36C of the tip part 31C has an uneven form. As illustrated in FIG. 13, the uneven form can be provided by configuring each individual one of the plurality of electrically conductive members 25C to be stepped with respect to an adjacent one of the plurality of electrically conductive members 25C. Alternatively, each step may be formed by two or more adjacent ones of the plurality of electrically conductive members 25C. With the uneven form illustrated in FIG. 13, the tip surface 36C has more non-continuous points than does a configuration having the uneven form illustrated in FIG. 11. As such, with the discharge electrode 21C, it is possible to cause adhered matter formed by electric discharge to be even less likely to adhere to the discharge electrode 21C.

Embodiment 4

The following description will discuss Embodiment 4 of the present invention with reference to FIGS. 14 to 20. For convenience, members similar in function to those described in Embodiments 1 through 3 will be given the same reference signs, and their description will be omitted.

Figure 14:
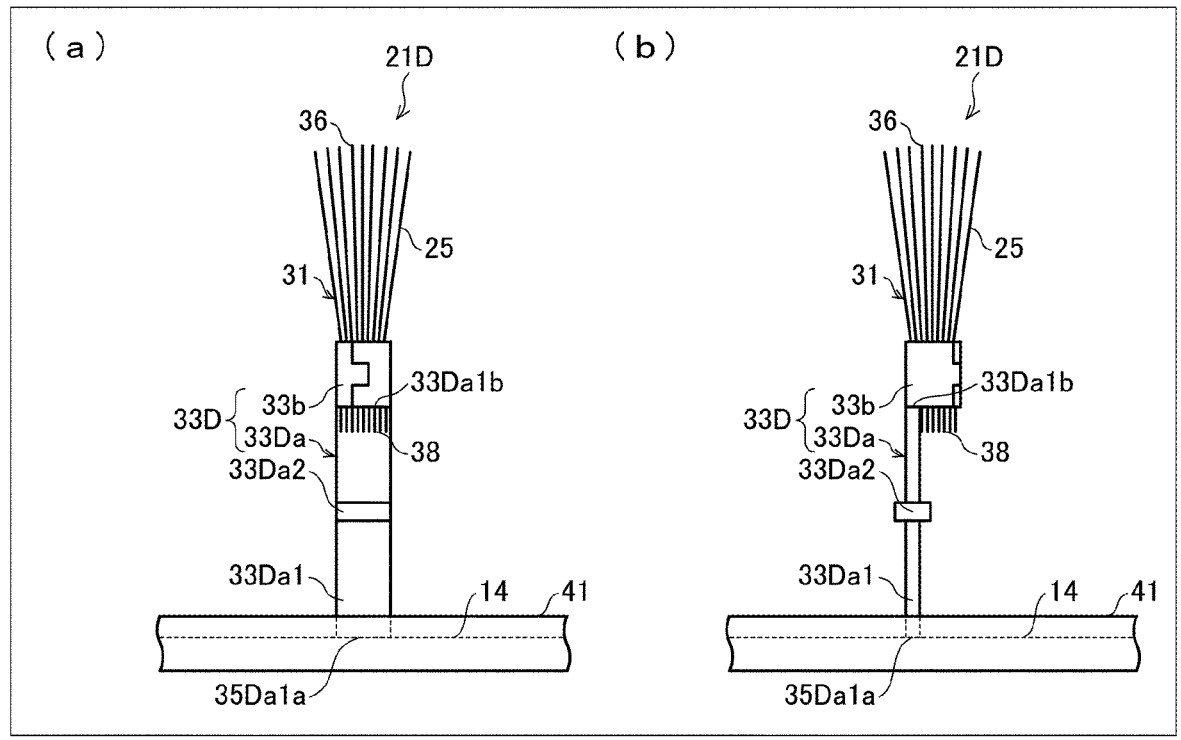
FIG. 14 is a diagram illustrating a configuration of (i) discharge electrodes of an ion generating device in accordance with Embodiment 4 and (ii) a vicinity of the discharge electrodes.

FIG. 14 illustrates a configuration of (i) a discharge electrode of an ion generating device in accordance with Embodiment 4 and (ii) a vicinity of the discharge electrode. (a) of FIG. 14 is an elevational view of the configuration, and (b) of FIG. 14 is a side view of the configuration.

The ion generating device 1 may include, instead of discharge electrodes 21 and 22 (see FIG. 3 and FIG. 4), discharge electrodes 21D and 21D. Aside from the discharge electrodes 21D and 21D, the ion generating device 1 in accordance with Embodiment 4 is configurationally similar to the ion generating device 1 described in Embodiment 1.

The discharge electrode 21D includes, instead of the base end part 33 (see FIG. 3 and FIG. 4), a base end part 33D. The base end part 33D differs from the base end part 33 by including a mounting part 33Da instead of the mounting part 33a (see FIG. 3 and FIG. 4). The discharge electrode 21D is otherwise configurationally similar to the discharge electrode 21.

Note that a base end surface (a surface on a side away from the tip surface 36) of the tip part 31 is here referred to as a base end surface 38. The base end surface 38 is on a lower side of the tip part 31 which lower side is near the binding part 33b.

The mounting part 33Da includes an extending part 33Da1 and a structure 33Da2. The extending part 33Da1 and the structure 33Da2 can be made from the same metallic material.

The extending part 33Da1 extends from (i) a base end part 33Da1a which is in contact with the ion generating element substrate 14 to (ii) a connection end 33Da1b at which the extending part 33Da1 connects to the binding part 33b. In other words, the extending part 33Da1 is a part which supports the binding part 33b and the tip part 31.

The structure 33Da2 is provided to the extending part 33Da1 so as to be partway between the base end part 33Da1a and the connection end 33Da1b. The structure 33Da2 prevents resin material which is in a non-cured liquid state (i.e., material which becomes the insulating sealing member 41) from creeping up the extending part 33Da1 when the discharge electrode 21D is being mounted on the ion generating element substrate 14.

The structure 33Da2 has a shape which differs from that of the extending part 33Da1. As one example, the structure 33Da2 can have a protruding shape so as to protrude from both plate surfaces of the extending part 33Da1.

During production of the insulating sealing member 41, when the resin material in a liquid state (i.e., the material which becomes the insulating sealing member 41) is being cured by heating or the like, the resin material in a liquid state may creep up the extending part 33Da1 from a base end part 33Da1a side thereof.

If the resin material adheres to the base end surface 38 of the tip part 31, the resin material will permeate toward the tip surface 36 of the tip part 31 due to capillary action of the plurality of fine electrically conductive members 25.

If resin material which has permeated toward the tip surface 36 of the tip part 31 then cures, it will inhibit spreading of the plurality of linear electrically conductive members 25. This impairs the ion generating capability of the discharge electrode 21D. That is, the performance of the ion generating device 1 will be disadvantageously decreased.

With the discharge electrode 21D, the structure 33Da2 is provided to the extending part 33Da1 of the mounting part 33Da so as to be partway between the base end part 33Da1a and the connection end 33Da1b. Therefore, even in a case where the resin material creeps up the extending part 33Da1, the structure 33Da2 serves as an obstacle. This makes it possible to prevent the resin material from creeping upward past the structure 33Da2. As such, it is possible to prevent the resin material from adhering to the tip part 31. It is therefore possible to prevent a decrease in the ion generating capability of the discharge electrode 21D. In other words, it is possible to prevent a decrease in the performance of the ion generating device 1.

The structure 33Da2 is preferably provided to the extending part 33Da1 so as to be higher than a surface of the resin material (i.e., higher than the surface of the insulating sealing member 41). This makes it possible for the structure 33Da2 to reliably stop the resin material from creeping up.

Furthermore, in some cases, the base end surface 38 of the tip part 31 may protrude further downward than a bottom end surface of the binding part 33b. In such a case, the structure 33Da2 is preferably provided to the extending part 33Da1 so as to be lower than the base end surface 38 of the tip part 31. This makes it possible for the structure 33Da2 to reliably prevent resin material which has creeped up the extending part 33Da1 from adhering to the base end surface 38 of the tip part 31.

The structure need only be a structure which serves as an obstacle to the resin material creeping up. The structure can have a variety of shapes, such as a protrusion from the extending part, a depression in the extending part, or an opening provided to the extending part. Some examples of variations of the structure 33Da2 are discussed below.

Note that the structures of the various variations are each provided to a position which is similar to the position of the structure 33Da2 on the extending part 33Da1.

(Variation 1)

Figure 15:
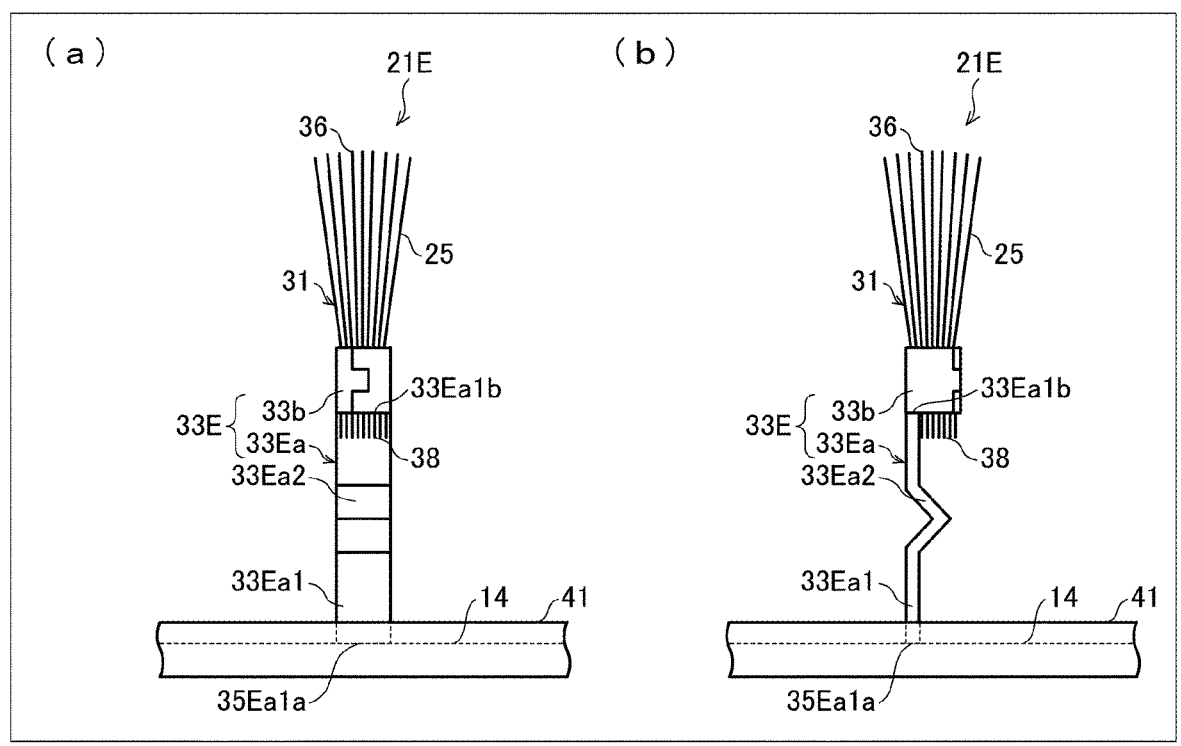
FIG. 15 is a diagram illustrating a configuration of (i) a discharge electrode in accordance with Variation 1 and (ii) a vicinity thereof, Variation 1 being a variation of the discharge electrode illustrated in FIG. 14.

FIG. 15 illustrates a configuration of (i) a discharge electrode 21E in accordance with Variation 1 and (ii) a vicinity thereof, Variation 1 being a variation of the discharge electrode 21D in accordance with Embodiment 4. (a) of FIG. 15 is an elevational view of the configuration, and (b) of FIG. 15 is a side view of the configuration.

The discharge electrode 21E includes, instead of the base end part 33D (see FIG. 14), a base end part 33E. The base end part 33E differs from the base end part 33D by including a mounting part 33Ea instead of the mounting part 33Da (see FIG. 14). The discharge electrode 21E is otherwise configurationally similar to the discharge electrode 21D.

The mounting part 33Ea includes an extending part 33Ea1 and a structure 33Ea2. The extending part 33Ea1 and the structure 33Ea2 can be made from the same metallic material. The structure 33Ea2 is provided to the extending part 33Ea 1 of the mounting part 33Ea so as to be partway between a base end part 33Ea1a and a connection end 33Ea1b.

The structure 33Ea2 forms a mountain-like protrusion in one plate surface of the extending part 33Ea1 and a mountain-like depression in the other plate surface of the extending part 33Ea1. The shape of the structure 33Ea2 serves as an obstacle to the resin material creeping up and makes it possible to prevent the resin material from creeping up to portions of the extending part 33Ea 1 above the structure 33Ea2.

(Variation 2)

Figure 16:
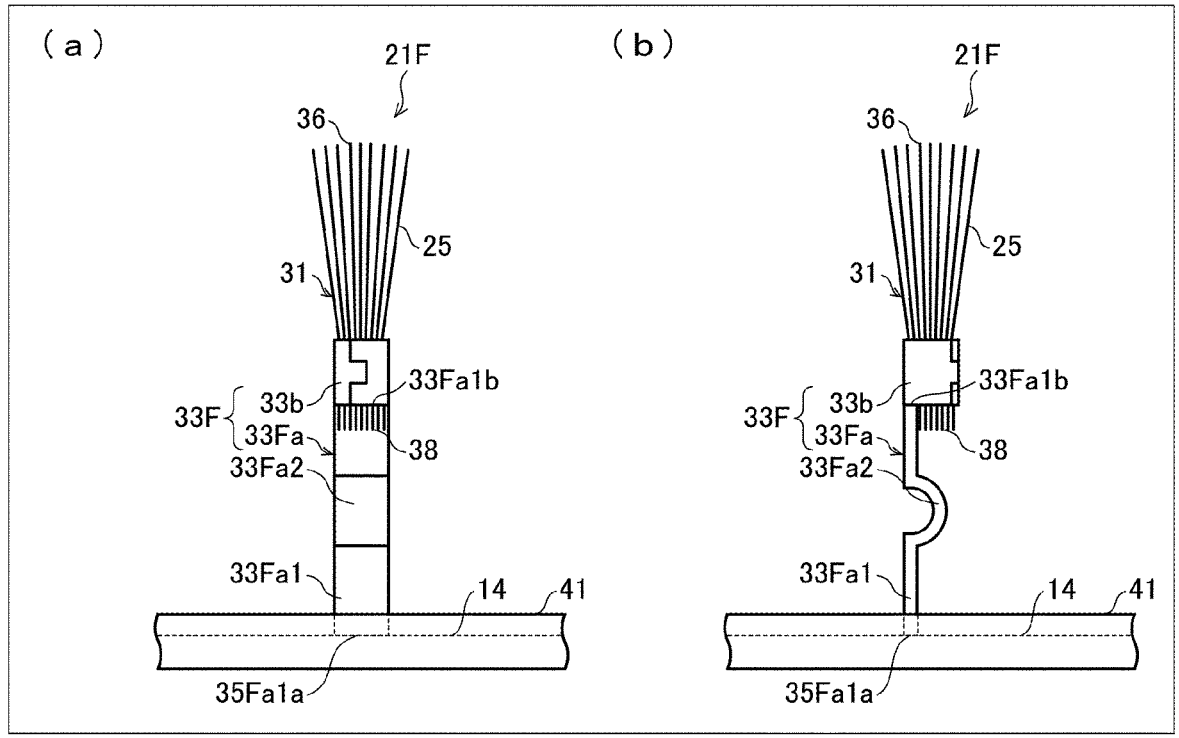
FIG. 16 is a diagram illustrating a configuration of (i) a discharge electrode in accordance with Variation 2 and (ii) a vicinity thereof, Variation 2 being a variation of the discharge electrode illustrated in FIG. 14.

FIG. 16 illustrates a configuration of (i) a discharge electrode 21F in accordance with Variation 2 and (ii) a vicinity thereof, Variation 2 being a variation of the discharge electrode 21D in accordance with Embodiment 4. (a) of FIG. 16 is an elevational view of the configuration, and (b) of FIG. 16 is a side view of the configuration.

The discharge electrode 21F includes, instead of the base end part 33D (see FIG. 14), a base end part 33F. The base end part 33F differs from the base end part 33D by including a mounting part 33Fa instead of the mounting part 33Da (see FIG. 14). The discharge electrode 21F is otherwise configurationally similar to the discharge electrode 21D.

The mounting part 33Fa includes an extending part 33Fa1 and a structure 33Fa2. The extending part 33Fa1 and the structure 33Fa2 can be made from the same metallic material. The structure 33Fa2 is provided to the extending part 33Fa 1 of the mounting part 33Fa so as to be partway between a base end part 33Fa1a and a connection end 33Fa1b.

The structure 33Fa2 forms a curved protrusion in one plate surface of the extending part 33Ea1 and a curved depression in the other plate surface of the extending part 33Ea1. The shape of the structure 33Fa2 serves as an obstacle to the resin material creeping up and makes it possible to prevent the resin material from creeping up to portions of the extending part 33Fa 1 higher than the structure 33Fa2.

(Variation 3)

Figure 17:
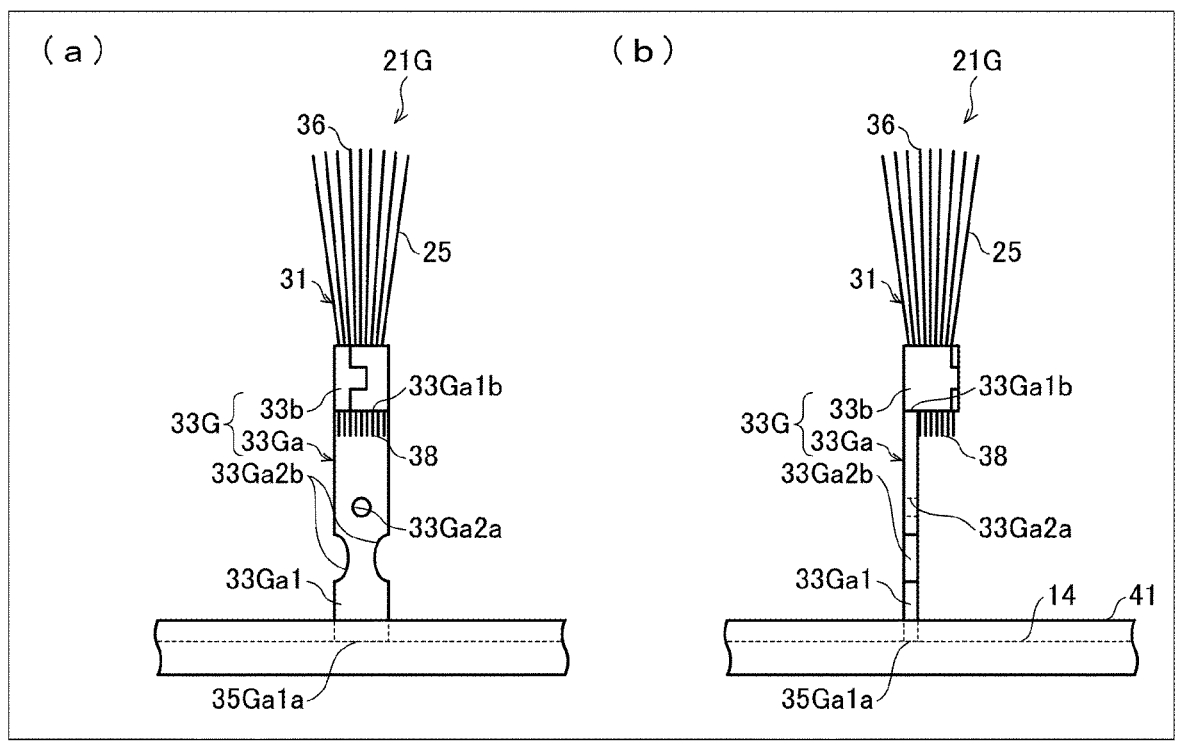
FIG. 17 is a diagram illustrating a configuration of (i) a discharge electrode in accordance with Variation 3 and (ii) a vicinity thereof, Variation 3 being a variation of the discharge electrode illustrated in FIG. 14.

FIG. 17 illustrates a configuration of (i) a discharge electrode 21G in accordance with Variation 3 and (ii) a vicinity thereof, Variation 3 being a variation of the discharge electrode 21D in accordance with Embodiment 4. (a) of FIG. 17 is an elevational view of the configuration, and (b) of FIG. 17 is a side view of the configuration.

The discharge electrode 21G includes, instead of the base end part 33D (see FIG. 14), a base end part 33G. The base end part 33G differs from the base end part 33D by including a mounting part 33Ga instead of the mounting part 33Da (see FIG. 14). The discharge electrode 21G is otherwise configurationally similar to the discharge electrode 21D.

The mounting part 33Ga includes an extending part 33Ga1 and structures 33Ga2a and Ga2b. The structures 33Ga2a and 33Ga2b are each provided to the extending part 33Ga1 of the mounting part 33Ga so as to be partway between a base end part 33Ga1a and a connection end 33Ga1b.

The structure 33Ga2a is an opening formed in the extending part 33Ga 1. The structures 33Ga2b are each a curved depression formed in a respective one of two lateral surfaces of the extending part 33Ga1, which lateral surfaces connect the two plate surfaces of the extending part 33Ga 1. The structures 33Ga2b are each a depression formed in a respective one of the two lateral surfaces of the extending part 33Ga1 so as not to reach a point midway between the two lateral surfaces. The two structures 33Ga2b are each formed in a respective one of the two lateral surfaces of the extending part 33Ga1 so as to be symmetrical.

The shapes of the structures 33Ga2a and 33Ga2b serve as obstacles to the resin material creeping up and make it possible to prevent the resin material from creeping up to portions of the extending part 33Ga1 higher than the structures 33Ga2a and 33Ga2b.

(Variation 4)

Figure 18:
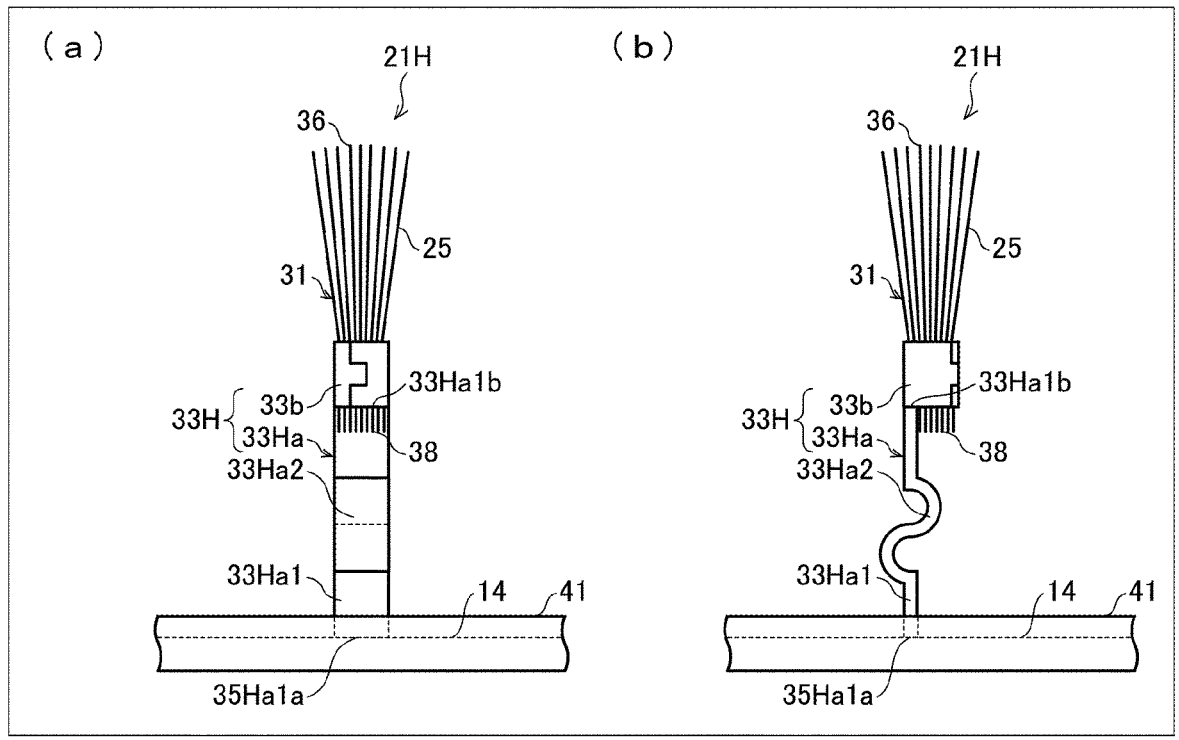
FIG. 18 is a diagram illustrating a configuration of (i) a discharge electrode in accordance with Variation 4 and (ii) a vicinity thereof, Variation 4 being a variation of the discharge electrode illustrated in FIG. 14.

FIG. 18 illustrates a configuration of (i) a discharge electrode 21H in accordance with Variation 4 and (ii) a vicinity thereof, Variation 4 being a variation of the discharge electrode 21D in accordance with Embodiment 4. (a) of FIG. 18 is an elevational view of the configuration, and (b) of FIG. 18 is a side view of the configuration.

The discharge electrode 21H includes, instead of the base end part 33D (see FIG. 14), a base end part 33H. The base end part 33H differs from the base end part 33D by including a mounting part 33Ha instead of the mounting part 33Da (see FIG. 14). The discharge electrode 21H is otherwise configurationally similar to the discharge electrode 21D.

The mounting part 33Ha includes an extending part 33Ha1 and a structure 33Ha2. The extending part 33Ha1 and the structure 33Ha2 can be made from the same metallic material. The structure 33Ha2 is provided to the extending part 33Ha 1 of the mounting part 33Ha so as to be partway between a base end part 33Ha1a and a connection end 33Ha1b.

The structure 33Ha2 has a first curved part and a second curved part which are provided in a continuous manner. The first curved part of the structure 33Ha2 forms a curved protrusion in one plate surface of the extending part 33Ea1 and a curved depression in the other plate surface of the extending part 33Ha1. The second curved part of the structure 33Ha2 forms a curved depression in the one plate surface of the extending part 33Ea1 and a curved protrusion in the other plate surface of the extending part 33Ea1.

The shape of the structure 33Ha2 serves as an obstacle to the resin material creeping up and makes it possible to prevent the resin material from creeping up to portions of the extending part 33Ha1 higher than the structure 33Ha2.

(Variation 5)

Figure 19:
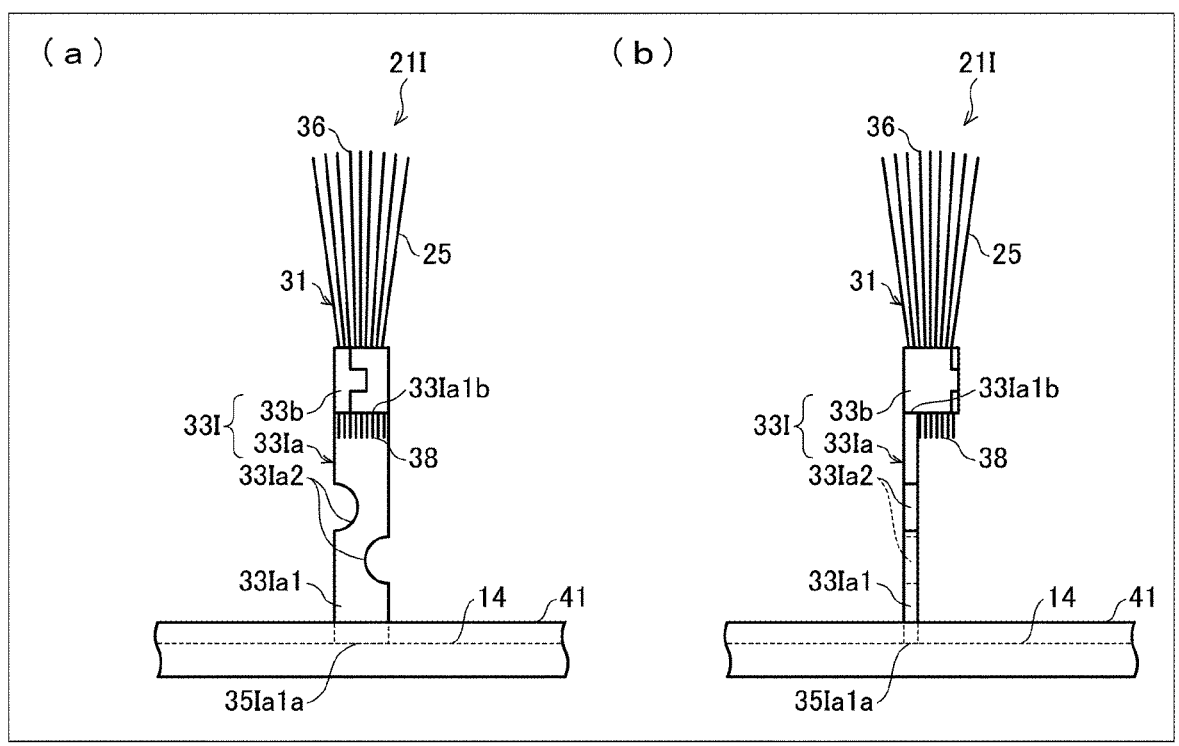
FIG. 19 is a diagram illustrating a configuration of (i) a discharge electrode in accordance with Variation 5 and (ii) a vicinity thereof, Variation 5 being a variation of the discharge electrode illustrated in FIG. 14.

FIG. 19 illustrates a configuration of (i) a discharge electrode 21I in accordance with Variation 5 and (ii) a vicinity thereof, Variation 5 being a variation of the discharge electrode 21D in accordance with Embodiment 4. (a) of FIG. 19 is an elevational view of the configuration, and (b) of FIG. 19 is a side view of the configuration.

The discharge electrode 21I includes, instead of the base end part 33D (see FIG. 14), a base end part 33I. The base end part 33I differs from the base end part 33D by including a mounting part 33Ia instead of the mounting part 33Da (see FIG. 14). The discharge electrode 21I is otherwise configurationally similar to the discharge electrode 21D.

The mounting part 33Ia includes an extending part 33Ia1 and structures 33Ia2. The structures 33Ia2 are provided to the extending part 33Ia1 of the mounting part 33Ia so as to be partway between a base end part 33Ia1$a$ and a connection end 33Ia1$b$.

The structures 33Ia 2 are each a curved depression formed in a respective one of two lateral surfaces of the extending part 33Ia1. The structures 33Ia 2 are each a depression formed in a respective one of the two lateral surfaces of the extending part 33Ia1 so as to extend past a point midway between the two lateral surfaces. The two structures 33Ia 2 are formed in respective ones of the two lateral surfaces so as to be staggered along an extension direction of the extending part 33Ia1 in a non-symmetrical manner.

The shape of the structures 33Ia 2 serves as an obstacle to the resin material creeping up and makes it possible to prevent the resin material from creeping up to portions of the extending part 33Ia1 higher than the structures 33Ia 2.

(Variation 6)

Figure 20:
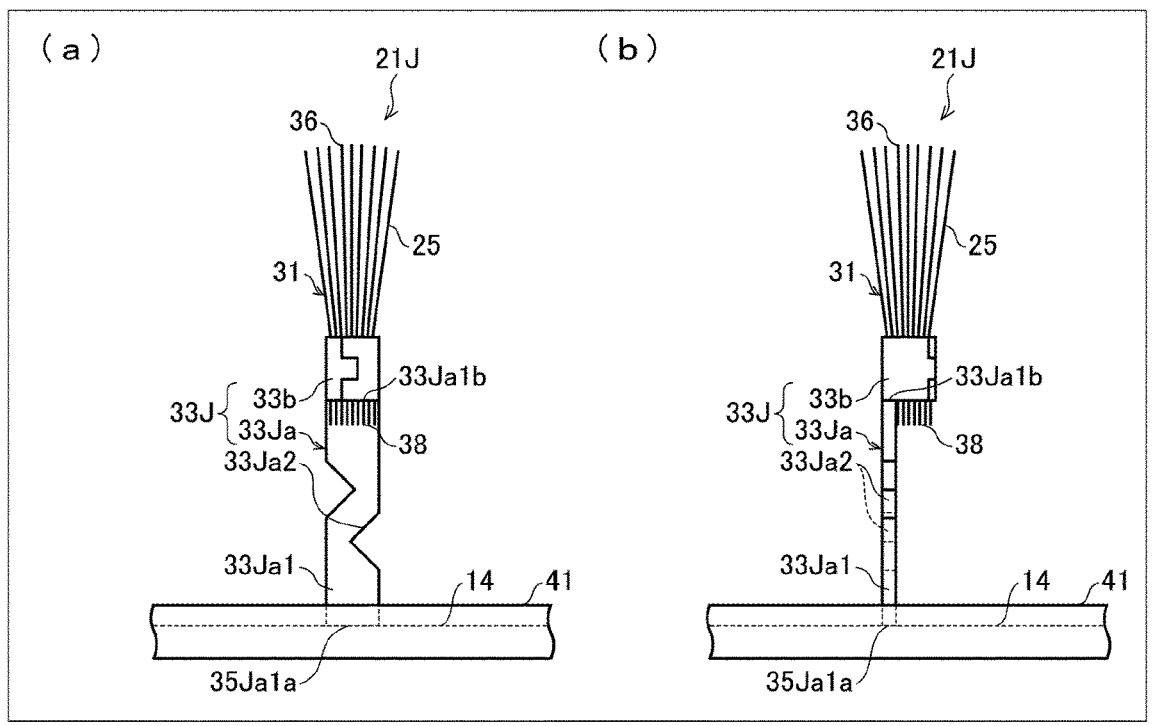
FIG. 20 is a diagram illustrating a configuration of (i) a discharge electrode in accordance with Variation 6 and (ii) a vicinity thereof, Variation 6 being a variation of the discharge electrode illustrated in FIG. 14.

FIG. 20 illustrates a configuration of (i) a discharge electrode 21J in accordance with Variation 6 and (ii) a vicinity thereof, Variation 6 being a variation of the discharge electrode 21D in accordance with Embodiment 4. (a) of FIG. 20 is an elevational view of the configuration, and (b) of FIG. 20 is a side view of the configuration.

The discharge electrode 21J includes, instead of the base end part 33D (see FIG. 14), a base end part 33J. The base end part 33J differs from the base end part 33D by including a mounting part 33Ja instead of the mounting part 33Da (see FIG. 14). The discharge electrode 21J is otherwise configurationally similar to the discharge electrode 21D.

The mounting part 33Ja includes an extending part 33Ja1 and structures 33Ja2. The structures 33Ja2 are provided to the extending part 33Ja 1 of the mounting part 33Ja so as to be partway between a base end part 33Ja1$a$ and a connection end 33Ja1$b$.

The structures 33Ja2 are each a mountain-shaped depression formed in a respective one of two lateral surfaces of the extending part 33Ja1. The structures 33Ja2 are each a depression formed in a respective one of the two lateral surfaces of the extending part 33Ja1 so as to extend past a point midway between the two lateral surfaces. The two structures 33Ja2 are formed in respective ones of the two lateral surfaces so as to be staggered along an extension direction of the extending part 33Ja1 in a non-symmetrical manner.

The shape of the structures 33Ja2 serves as an obstacle to the resin material creeping up and makes it possible to prevent the resin material from creeping up to portions of the extending part 33Ja1 higher than the structures 33Ja2.

Embodiment 5

Figure 21:
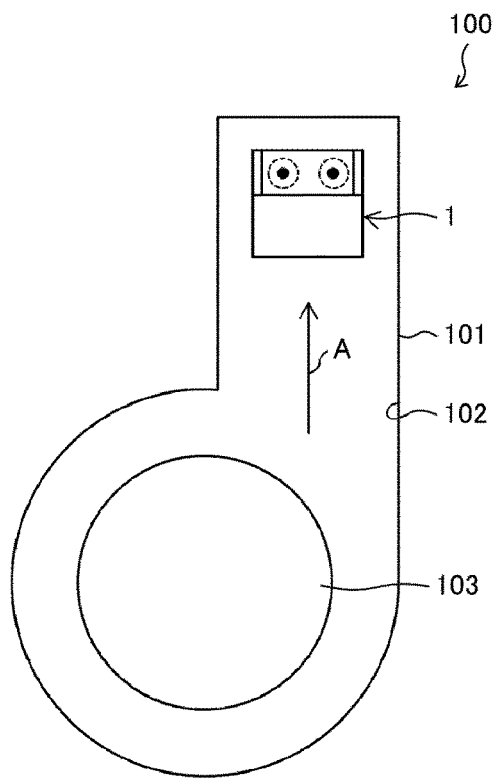
FIG. 21 is a plan view illustrating an example of a configuration of an inside of an electrical apparatus in accordance with Embodiment 5 of the present invention.

Embodiment 5 of the present invention is described below with reference to FIG. 21. Embodiment 5 describes an electrical apparatus including an ion generating device. FIG. 21 is a plan view showing an example of a configuration of an inside of an electrical apparatus 100 of Embodiment 5. A configuration of the electrical apparatus 100 is described with reference to FIG. 21.

As illustrated in FIG. 21, the electrical apparatus 100 has a casing 101 for a fan (hereinafter referred to as a "fan casing 101") part of which is provided with the ion generating device 1, the fan casing 101 constituting an air flow path 102, which is a path through which to guide, to an outside of the ion generating device 1, ions generated by the ion generating device 1.

Thus, in the air flow path 102, the ion generating device 1 and an air sending device 103 for sending gas, by which the ions generated by the ion generating device 1 are carried, are provided. The ion generating device 1 is provided on a downstream side of an air sending direction A in which the air sending device 103 sends air. In other words, the air sending device 103 sends a gas in the air sending direction A to the ion generating device 1 and the discharge electrodes 21 and 22. Note that the air sending device 103 can be a sirocco fan, a crossflow fan, or another fan.

The ion generating device 1 can be integrally incorporated into the electrical apparatus 100 or can be provided so as to be detachable and attachable with respect to the electrical apparatus 100. The ion generating device 1 which is provided so as to be detachable and attachable with respect to the electrical apparatus 100 allows the ion generating device 1 to be replaced and cleaned. This facilitates maintenance of the electrical apparatus 100.

The electrical apparatus 100 is not particularly limited in type and can be, for example, an ion generator, an air conditioner, a dehumidification machine, a humidifier, an air cleaner, a fan heater, or another apparatus. The electrical apparatus 100 can be an electrical apparatus for use in a house or an electrical apparatus for automotive use. The electrical apparatus 100 is suitably used to condition air in, for example, a house, a room of a building, a hospital room, a vehicle, an airplane, or a vessel.

As described earlier, a mounting part 33$a$ can be formed so as to be plate-like. In a case where the mounting part 33$a$ is plate-like, an orientation of a plate surface of the mounting part 33$a$, which is plate-like, is preferably set in view of the air sending direction A in the electrical apparatus 100.

Note that in a case where the discharge electrodes of the electrical apparatus 100 are to be cleaned, the ion generating device 1 is removed and then the discharge electrodes within the ion generating device 1 are cleaned. Discussed in the following Embodiment 6 is an example in which discharge electrodes can be cleaned without removing the ion generating device 1 from the electrical apparatus 100.

Embodiment 6

The following description will discuss Embodiment 6 of the present invention with reference to FIGS. 22 to 26. For convenience, members similar in function to those described in Embodiments 1 through 5 will be given the same reference signs, and their description will be omitted.

(Overall Configuration of Ion Generating Device 2)

Figure 22:
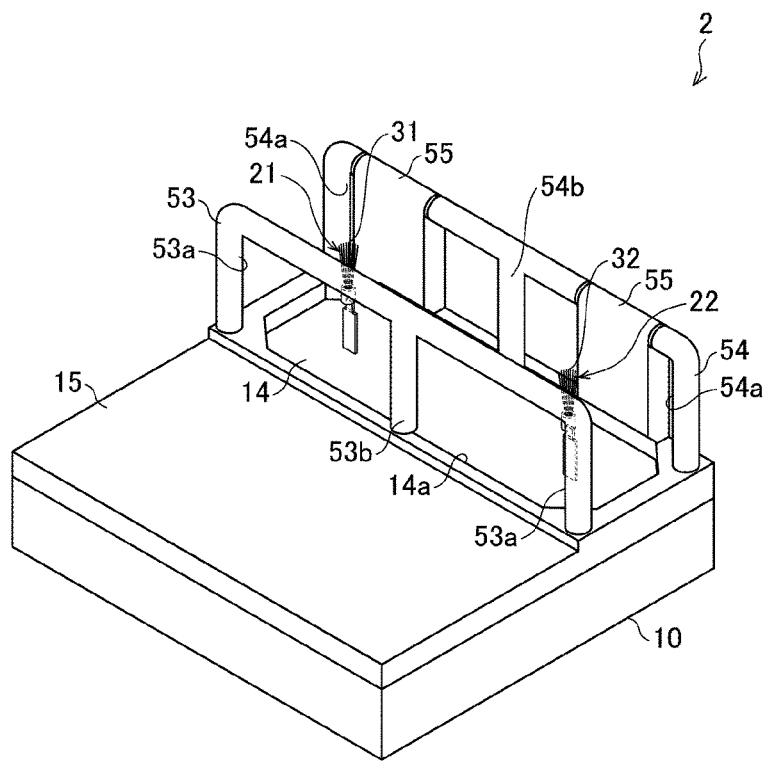
FIG. 22 is a perspective view schematically illustrating a configuration of an ion generating device in accordance with Embodiment 6 of the present invention.
Figure 22:
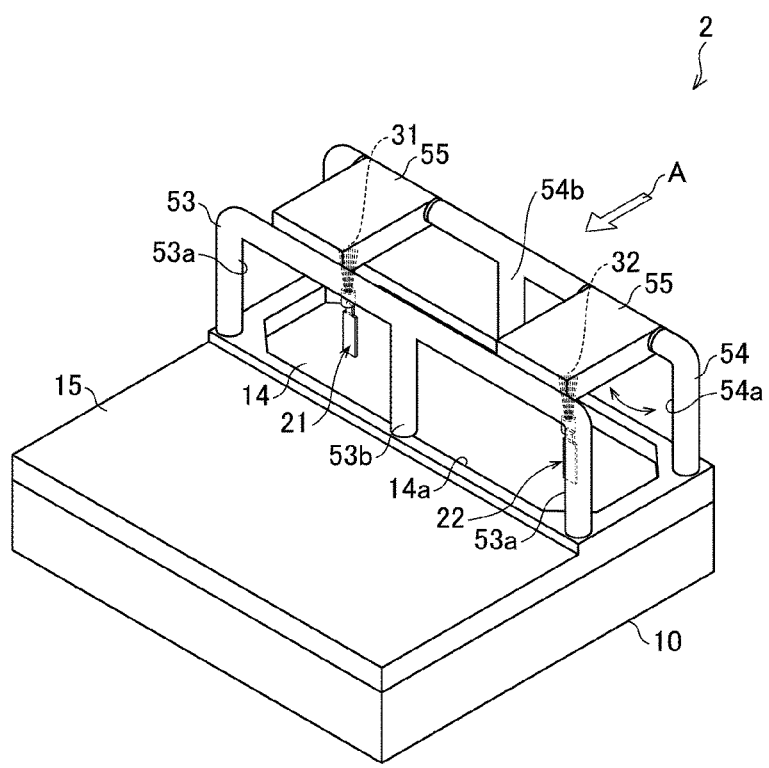

FIG. 22 is a perspective view schematically illustrating an ion generating device 2. (a) of FIG. 22 illustrates the ion generating device 2 in a state prior to ion generation (prior to ventilation). (b) of FIG. 22 illustrates the ion generating device 2 in a state during ion generation (during ventilation).

As illustrated in (a) and (b) of FIG. 22, the ion generating device 2 has a configuration which is basically the same as that of the ion generating device 1 of Embodiment 1. The ion generating device 2 differs from the ion generating device 1 with regards to where protective plates 53 and 54 (protruding members) are formed, and with regards to the shape of the protective plates 53 and 54. Furthermore, the ion generating device 2 differs from the ion generating device 1 by including cleaning plates 55 (cleaning members) for cleaning tip parts 31 and 32 (discharging sections) of discharge electrodes 21 and 22.

As illustrated in FIG. 22, a gas, such as air, which carries ions released from the discharge electrodes 21 and 22 is sent in a front-to-rear direction of the ion generating device 2, similarly to the ion generating device 1. Note that, similarly to Embodiments 1 to 5, a direction in which the ion-carrying gas is sent is referred to as an air sending direction A. The air sending direction A is the same in drawings other than FIG. 22, such as FIG. 23.

Figure 23:
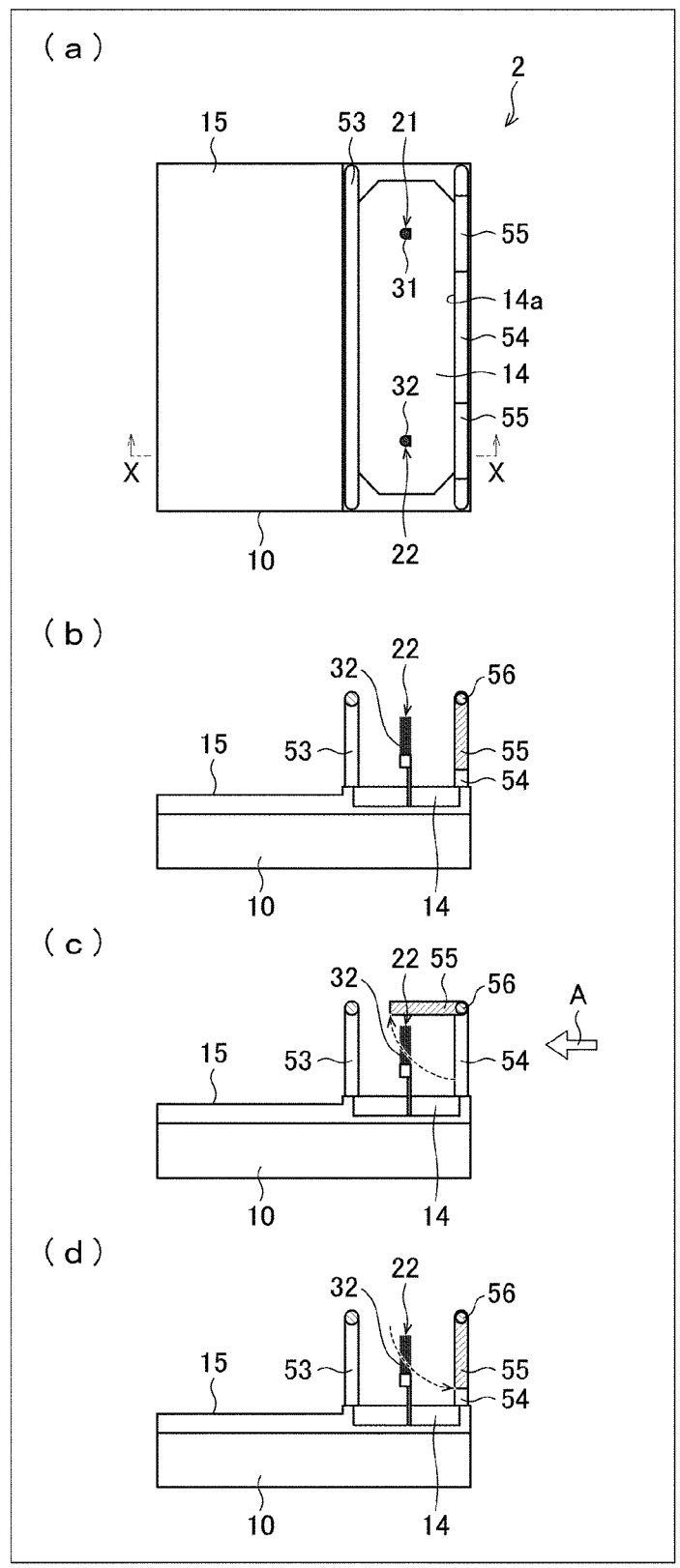
FIG. 23 is a diagram illustrating how the discharge electrodes of the ion generating device illustrated in FIG. 22 are cleaned.

(a) of FIG. 23 is a plan view illustrating the ion generating device 2. (b) of FIG. 23 is a cross-sectional view taken along line X-X of (a) of FIG. 23. (c) and (d) of FIG. 23 are both diagrams illustrating how the cleaning plates 55 operate during cleaning of the discharge electrodes 21 and 22.

An ion generating element substrate 14, in which the discharge electrodes 21 and 22 protrude, is provided in an end of a front part (i.e., on a side from which air is introduced) of an upper surface of a case 10, which is quadrangular. The protective plates 53 and 54 are provided near to the discharge electrodes 21 and 22 so as to protrude from the front part (on the side from which air is introduced) of the upper surface of the case 10. In this way, the protective plates 53 and 54 protect the discharge electrodes 21 and 22, similarly to the protective plates 51 and 52 of the ion generating device 1 of Embodiment 1.

The protective plates 53 and 54 are juxtaposed to each other while the discharge electrodes 21 and 22 are sandwiched therebetween in a direction orthogonal to a longer side direction of the ion generating element substrate 14 (i.e., orthogonal to a direction parallel to the long side 14a of the ion generating element substrate 14), which longer side direction is the direction in which the discharge electrodes 21 and 22 are arranged. The protective plates 53 and 54 are arranged such that the protective plate 54 is upwind of the protective plate 53 along the direction in which air is introduced (along the direction of the arrow A).

The protective plates 53 and 54 have a height whose maximum value is greater than a height of the discharge electrodes 21 and 22. The protective plates 53 and 54 vertically protrude, in an upper part of the lid 15, or by being integrally molded with the lid 15, so as to further protrude from the surface of the ion generating element substrate 14 than the tip parts 31 and 32 of the discharge electrodes 21 and 22.

With this arrangement, even in a case where the ion generating device 2 is, for example, overturned, the discharge electrodes 21 and 22 can be prevented from directly contacting an object, provided on an outside of the ion generating device 2, such as a placing base, so that the discharge electrodes 21 and 22 can be prevented from, for example, being broken by the contact.

Note here that the height of the protective plates 53 and 54 refers to a vertical length, i.e., a height from the surface of the lid 15 to an upper surface of the protective plate 53 as well as a height from the surface of lid 15 to an upper surface of the protective plate 54.

The height of the protective plates 53 and 54 is not particularly limited, provided that the protective plates 53 and 54 further protrude from the surface of the ion generating element substrate 14 than the tip parts 31 and 32 of the discharge electrodes 21 and 22. Note, however, that an increase in the height of the protective plates 53 and 54 makes the ion generating device 2 larger in size accordingly. Thus, the protective plates 53 and 54 desirably have a height that is great enough for the discharge electrodes 21 and 22 to be prevented from directly contacting the object, provided on the outside of the ion generating device 2, such as the placing base in a case where the ion generating device 2 is, for example, overturned.

The protective plates 53 and 54 are spaced from the discharge electrodes 21 and 22 so that a distance between (i) the discharge electrodes 21 and 22 and (ii) the protective plates 53 and 54 is longer than the length of the tip parts 31 and 32 of the discharge electrodes 21 and 22.

Thus, even in a case where the electrically conductive members 25 of the tip part 31 (FIG. 3) or the electrically conductive members 26 of the tip part 32 (FIG. 3) repel each other and the tip part 31 or 32 spreads, so that the electrically conductive members 25 or the electrically conductive members 26 lean at any angle, the electrically conductive members 25 and the electrically conductive members 26 do not directly contact the protective plates 53 and•54. This makes it possible to prevent occurrence of a leakage.

The protective plates 53 and 54 have openings 53a and 54a, respectively, which are formed in portions of the protective plates 53 and 54 which are opposite to the discharge electrodes 21 and 22. With this configuration, the protective plates 53 and 54 are structured so as to protect the discharge electrodes 21 and 22 while also allowing air to flow in the air sending direction A, through the openings 53a and 54a, to the discharge electrodes 21 and 22.

The protective plate 54, which is positioned upwind of the protective plate 53, is provided with the cleaning plates 55. Each of the cleaning plates 55 covers a respective one of the openings 54a and is supported at an upper end part of a respective one of the openings 54a, by a rotation shaft 56, such that each of the cleaning plates 55 can rotate freely. As illustrated in (b) of FIG. 22, in a state where the cleaning plates 55 are pushed by air sent in the air sending direction A and thereby rotated toward the protective plate 53, the air passes through the openings 54a and reaches the discharge electrodes 21 and 22.

Each of the cleaning plates 55 is, for example, a plate-like member molded from a resin such as plastic. Each of the cleaning plates 55 has a weight which allows the cleaning plates 55 to be rotated by air being blown thereon in the air sending direction A in the ion generating device 2. The resin material can be identical to or different from the material of the case. For example, the resin material can be a resin such as polyethylene, polypropylene, polystyrene, PTFE, polyvinyl chloride, ABS, acrylic, nylon, polyacetal, polybutylene terephthalate, polyethylene terephthalate, or polycarbonate. Polyacetal and nylon are suitable in terms of abrasion resistance. Note that the material of the cleaning plates 55 is not limited to the above materials. The material of the cleaning plates 55 need only be a material which is light enough to allow the cleaning plates 55 to be rotated by airflow and strong enough that the cleaning plates 55 can clean the tip parts 31 and 32 of the discharge electrodes 21 and 22 during rotation. For example, each of the cleaning plates 55 includes an upper end part 55a which is a center of rotation and a plate-like member having (i) an airflow receiving surface 55b which receives air being sent in the air sending direction A and (ii) a counter surface 55c, as illustrated in (a) and (b) of FIG. 25.

The two cleaning plates 55 each have a length such that, when they rotate toward the protective plate 53, they each come into contact with a respective one of the tip parts 31 and 32 of the discharge electrodes 21 and 22. With this configuration, when the two cleaning plates 55 rotate toward the protective plate 53, they come into contact with a respective one of the tip parts 31 and 32, brush away dust or dirt adhering to the tip parts 31 and 32, and thus clean the discharge electrodes 21 and 22.

Figure 25:
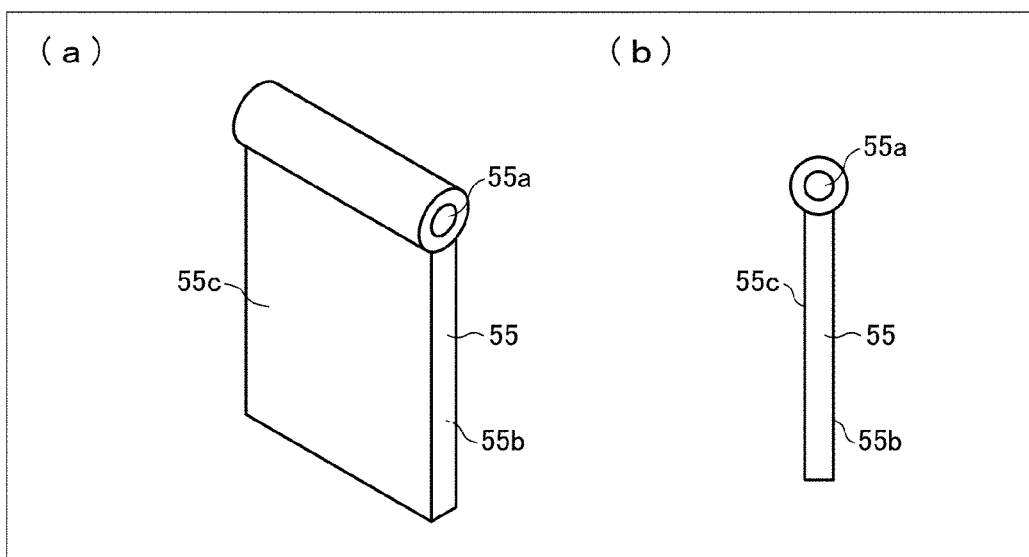
FIG. 25 is a diagram illustrating an example of a cleaning plate.

Note that the cleaning plates 55 are not limited to the shape illustrated in FIG. 25. The cleaning plates 55 may have any shape, provided that the cleaning plates 55 come into contact with a respective one of the tip parts 31 and 32 of the discharge electrodes 21 and 22 when the cleaning plates 55 rotate toward the protective plate 53. Other shapes of the cleaning plates are discussed later.

(Cleaning Action of Cleaning Plates 55)

The following description will discuss, with reference to (b) to (d) of FIG. 23, how the cleaning plates 55 clean the discharge electrodes 21 and 22.

Before the ion generating device 2 generates ions, the cleaning plates 55 are in standby in a position overlapping with the protective plate 54, as illustrated in (b) of FIG. 23. Once ion generation begins, air is sent in the air sending direction A, and the cleaning plates 55 rotate toward the protective plate 53 as illustrated in (c) of FIG. 23. While the air is being sent, the cleaning plates 55 remain in a state of being rotated to a position at which they are substantially parallel to the air sending direction A. While the cleaning plates 55 are in this state, ions generated by the discharge electrodes 21 and 22 are blown toward the protective plate 53 by the air being sent in the air sending direction A, and the ions are released to outside the ion generating device 2. Once the airflow in the air sending direction A is stopped, the weight of the cleaning plates 55 causes the cleaning plates 55 to rotate toward the protective plate 54 and back to their original positions, as illustrated in (d) of FIG. 23.

Note here that when the ion generating device 2 begins generating ions (when ventilation begins), as the cleaning plates 55 rotate, tip parts of the cleaning plates 55 come into contact with the tip parts 31 and 32 of the discharge electrodes 21 and 22, as illustrated in (b) and (c) of FIG. 23. Furthermore, when the ion generating device 2 stops generating ions (when ventilation stops), as the cleaning plates 55 rotate, the tip parts of the cleaning plates 55 come into contact with the tip parts 31 and 32 of the discharge electrodes 21 and 22, as illustrated in (c) and (d) of FIG. 23.

In this way, with the ion generating device 2, the discharge electrodes 21 and 22 are cleaned by the cleaning plates 55 coming into contact with the discharge electrodes 21 and 22 twice, i.e., when ion generation begins (when ventilation begins) and when ion generation stops (when ventilation stops).

As described above, it is necessary for the cleaning plates 55 to have a length such that the cleaning plates 55 come into contact with the tip parts 31 and 32 of the discharge electrodes 21 and 22 via rotational movement. The width of the cleaning plates 55 does not have to be so wide that the cleaning plates 55 completely cover respective ones of the openings 54a. The width of the cleaning plates 55 can be narrower than the width of the openings 54a, provided that the width of the cleaning plates 55 is enough to allow the cleaning plates 55 to receive the air being sent in the air sending direction A and be rotated thereby.

(Returning Action of Cleaning Plates 55)

Figure 24:
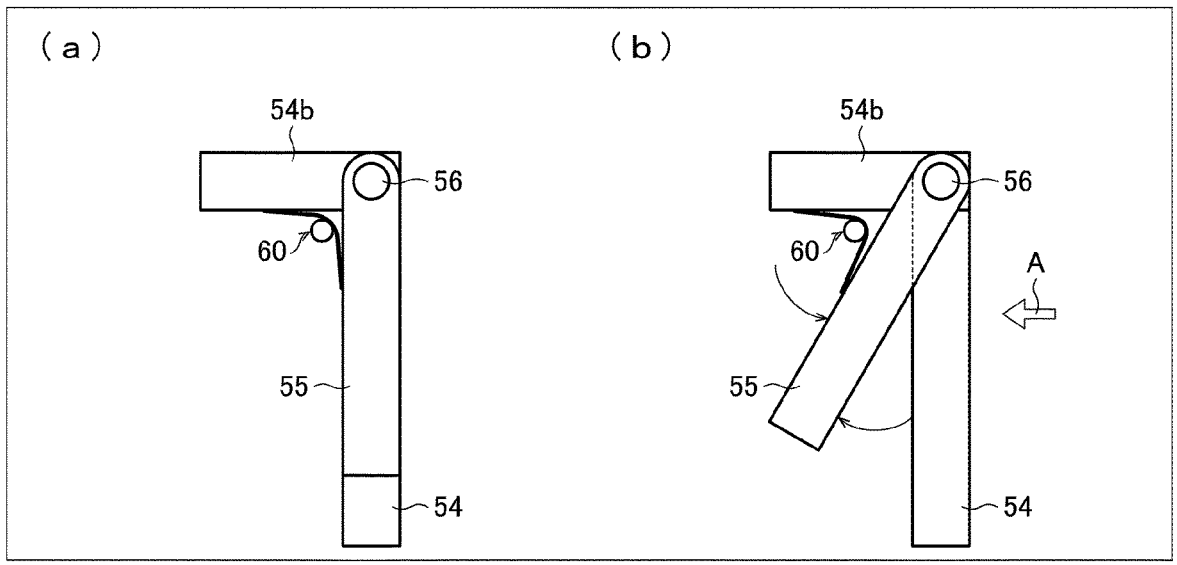
FIG. 24 is a diagram illustrating an example of a rotation mechanism of a cleaning plate for cleaning the discharge electrodes of the ion generating device illustrated in FIG. 22.

FIG. 23 illustrated an example in which the weight of the cleaning plates 55 caused the cleaning plates 55 to return to their original positions at the protective plate 54. Note however, that the cleaning plates 55 can be configured such that an actuating force causes them to return to their original positions at the protective plate 54. FIG. 24 is a diagram illustrating an example in which the cleaning plates 55 are returned to their original positions at the protective plate 54 by an actuating force. (a) of FIG. 24 illustrates one of the cleaning plates 55 in a standby state in a position overlapping with the protective plate 54. (b) of FIG. 24 illustrates one of the cleaning plates 55 in a state in which air sent in the air sending direction A causes the cleaning plate 55 to rotate against an actuating force acting in a direction opposite to the air sending direction A.

As illustrated in (a) and (b) of FIG. 24, a spring 60 is provided, as a member which applies an actuating force, between (i) an upper end part 54b of the protective plate 54, which upper end part 54b protrudes in the direction toward which the cleaning plates 55 rotate, and (ii) an upper end part side of each of the cleaning plates 55. The spring 60 applies an actuating force on each of the cleaning plates 55 in a direction opposite to the direction in which the cleaning plates 55 are rotated by airflow. Note that the actuating force applied by the spring 60 is of a magnitude that allows air sent in the air sending direction A to rotate the cleaning plates 55 toward the protective plate 53 such that the air reaches the discharge electrodes 21 and 22, as illustrated in (c) of FIG. 23. The magnitude of the actuating force also allows the cleaning plates 55 to stay in a rotated state.

Note that the spring 60 may be a coil spring, a plate spring, or the like. The spring 60 may be any type of spring, provided that it imparts the actuating force as described above. Furthermore, the spring 60 is not a limiting example of a means for applying the actuating force. The means for applying the actuating force need only be a mechanical mechanism that imparts an external force such that the cleaning plates 55 return to their original positions (standby positions at the protective plate 54) when the cleaning plates 55 are not subject to an external force due to air being sent.

As described above, providing the spring 60 makes it possible to prevent the cleaning plates 55 from moving from predetermined positions at the protective plate 54 (i.e., from standby positions) when ion generation has stopped (when ventilation has stopped). In other words, because the cleaning plates 55 will not move from their standby positions when there is no air being sent in the air sending direction A, the cleaning plates 55 will not rotate except when necessary (when ions are being generated). This configuration therefore brings about an effect of reducing damage to and deterioration of the discharge electrodes 21 and 22 by preventing the cleaning plates 55 from rotating unnecessarily and coming into contact with the discharge electrodes 21 and 22 more than necessary.

(Structure of Cleaning Plates)

Figure 26:
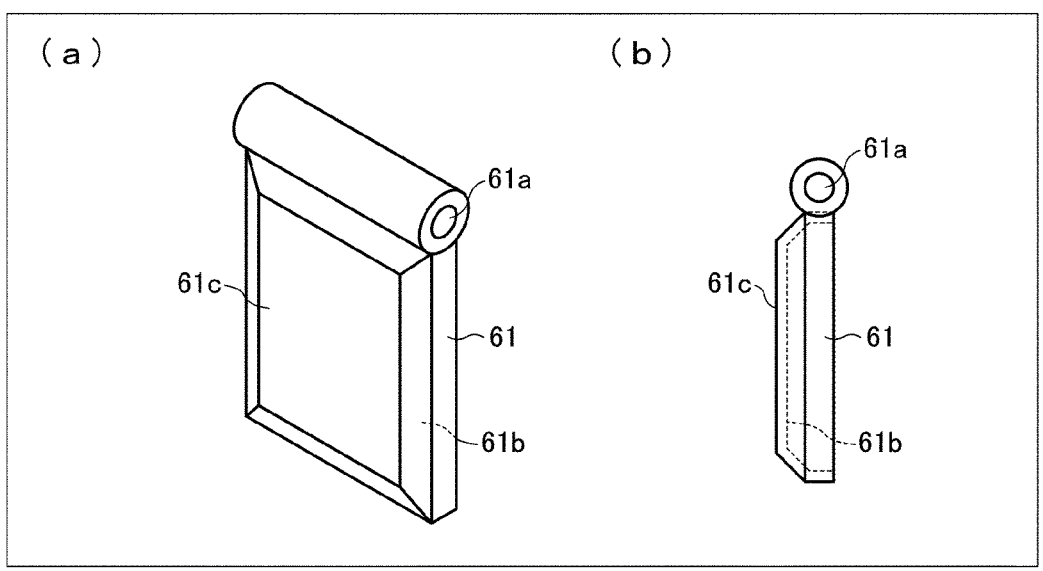
FIG. 26 is a diagram illustrating another example of a cleaning plate.

FIG. 25 is a diagram schematically illustrating the cleaning plates 55 illustrated in FIGS. 22 to 24. (a) of FIG. 25 is a perspective view, and (b) of FIG. 25 is a side view. FIG. 26 is a diagram schematically illustrating another example of a cleaning plate. (a) of FIG. 26 is a perspective view, and (b) of FIG. 26 is a side view.

As illustrated in FIG. 25, the airflow receiving surface 55b of each of the cleaning plates 55 is flat and can therefore receive airflow to a certain degree. However, in order to further receive airflow, it is preferable to use a cleaning plate 61 having a shape as illustrated in FIG. 26.

As illustrated in FIG. 26, the cleaning plate 61 includes an upper end part 61a, which is a center of rotation, and a member having (i) an airflow receiving surface 61b which receives air being sent in the air sending direction A, and (ii) a counter surface 61c. The airflow receiving surface 61b is depressed in the air sending direction A, and, correspondingly, the counter surface 61c protrudes in the air sending direction A. In this way, because the cleaning plate 61 has the airflow receiving surface 61b which is depressed, the cleaning plate 61 receives airflow better than the cleaning plates 55 of FIG. 25. The cleaning plate 61 can therefore be rotated by a smaller external force. This makes it possible to make the cleaning plate 61 lighter.

Note that it is preferable to carry out an antistatic treatment on the cleaning plates 55 and the cleaning plate 61. Using the cleaning plates 55 or the cleaning plate 61 which have been subjected to an antistatic treatment makes it possible to prevent dust or dirt from adhering to the cleaning plates 55 themselves or the cleaning plate 61 itself. For example, in a case where an antistatic treatment is not carried out on the cleaning plates 55 or the cleaning plate 61, there is a risk that dust or dirt brushed off the discharge electrodes 21 and 22 by the cleaning plates 55 or the cleaning plate 61 will adhere to the cleaning plates 55 or the cleaning plate 61. However, this risk does not occur with the cleaning plates 55 or the cleaning plate 61 which have been subjected to an antistatic treatment.

The external force applied by the air sent in the air sending direction A need only have at least a magnitude such that the external force can rotate the cleaning plates 55 or the cleaning plate 61. The external force preferably has at least a magnitude such that the external force pushes and spreads the plurality of linear electrically conductive members 25 and 26 of the tip parts 31 and 32 (FIG. 3) in a lateral direction (a direction orthogonal to the sending direction A). This makes it possible to efficiently generate ions generated by the discharge electrodes 21 and 22.

The force applied when returning the cleaning plates 55 or the cleaning plate 61 to their original positions (standby positions at the protective plate 54) preferably has at least a magnitude such that the force pushes and spreads the plurality of linear electrically conductive members 25 and 26 of the tip parts 31 and 32 (FIG. 3) in the lateral direction (the direction orthogonal to the sending direction A). This makes it possible to efficiently remove dust or dirt adhered to the discharge electrodes 21 and 22.

Note that, although Embodiment 6 discussed an example in which the cleaning plates 55 are provided to the protective plate 54, this example is non-limiting. The cleaning plates 55 can be provided at any position, provided that they are upwind of the discharge electrodes 21 and 22 in the air sending direction A, are driven by the air sent in the air sending direction A, and can come into contact with discharge sections of the discharge electrodes 21 and 22.

Furthermore, although plate-like cleaning members such as the cleaning plates 55 and the cleaning plate 61 were discussed as cleaning members for cleaning the discharge sections of the discharge electrodes 21 and 22, these examples are non-limiting, and the cleaning members may have other shapes.

[Recap]

A ion generating device 1 in accordance with Aspect 1 of the present invention is an ion generating device including: a discharge electrode 21•22 for generating ions by electric discharge, the discharge electrode 21•22 including (i) a tip part 31•32 having a plurality of linear electrically conductive members 25•26, (ii) a binding part 33b•34b for binding together respective base end parts of the plurality of linear electrically conductive members 25•26, and (iii) a mounting part 33a•34a for mounting the binding part 33b•34b on the ion generating device 1, the plurality of linear electrically conductive members 25•26 forming a tip surface 36•37 which is shaped so as to have a longer dimension direction and a shorter dimension direction, an air sending direction A, in which gas is sent to the discharge electrode 21•22 in order to carry the ions, being nonparallel to the longer dimension direction of the tip surface 36•37.

In comparison to a configuration in which the longer dimension direction of the tip surface is parallel to the air sending direction, the above configuration allows the tip surface to receive airflow even more efficiently and therefore allows the discharge electrode to more efficiently release and spread ions from the tip surface. This makes it possible to obtain an ion generating device which can release ions efficiently.

In Aspect 2 of the present invention, the ion generating device 1 of Aspect 1 can be arranged such that the longer dimension direction of the tip surface 36•37 is perpendicular to the air sending direction A. This configuration makes it possible for the tip surface to receive airflow even more efficiently and therefore makes it possible to release and spread ions more from the tip surface more efficiently.

In Aspect 3 of the present invention, the ion generating device 1 of Aspect 1 or 2 can be arranged such that: the discharge electrode 21•22 includes two discharge electrodes; and a direction along which the two discharge electrodes 21•22 are arranged is perpendicular to the air sending direction A. With the above configuration, more air is sent between the two discharge electrodes. This makes it possible for the tip surface to receive airflow efficiently and therefore makes it possible to release and spread ions more from the tip surface more efficiently.

In Aspect 4 of the present invention, the ion generating device 1 of Aspects 1 to 3 is preferably arranged such that the tip surface 36B has an edge portion which has an uneven form. With the above configuration, electric discharge is particularly concentrated to vertices of protrusions in the uneven form. As such, even in a case where adhered matter formed by electric discharge, the adhered matter is formed at vertices of protrusions and is unlikely to be formed between vertices of protruding portions. Therefore, even in a case where the tip part is energized over a long period, it is possible to maintain a state where individual ones of the plurality of linear electrically conductive members are separate from each other. As such, the above discharge electrode makes it possible to prevent a decrease in the efficiency of the release of ions. In other words, the discharge electrode makes it possible to increase ion release efficiency in a case where ions are released over a long period.

In Aspect 5 of the present invention, the ion generating device 1 of Aspects 1 to 4 can be arranged so as to further include a resin (insulating sealing member 41) with which to seal a base end part 33Da1 of the mounting part 33Da, the mounting part 33Da including (i) an extending part 33Da1 which extends from the base end part 33Da1a of the mounting part 33Da to a connection end 33Da1b of the mounting part 33Da at which connection end 33Da1b the mounting part 33Da connects to the binding part 33b and (ii) a structure 33Da2 which is provided to the extending part 33Da1 and has a shape differing from that of the extending part 33Da1.

With the above configuration, even in a case where the resin creeps up along the extending part before curing, the structure having a shape differing from that of the extending part serves as an obstacle. This makes it possible to prevent the resin from creeping to above the structure before curing. As such, it is possible to prevent the resin which has not cured from adhering to the plurality of linear electrically conductive members. The above configuration therefore makes it possible to prevent a decrease in the ion generating capability of the discharge electrode.

In Aspect 6 of the present invention, the ion generating device 1 of Aspect 5 can be arranged such that the structure 33Da2 to 33Ja2 includes at least one of a protrusion from the extending part, a depression in the extending part, and an opening formed in the extending part. With this configuration, the structure serves as an obstacle to the resin creeping up before curing. As such, it is possible to prevent the resin from (i) creeping to above the structure before curing and (ii) adhering to the plurality of linear electrically conductive members.

A method, of Aspect 7 of the present invention, for producing an ion generating device is a method for producing the ion generating device of Aspect 6, including the step of: forming the resin (insulating sealing member 41) by curing a liquid resin material. With this method, it is possible to form the resin (insulating sealing member 41) in a manner such that the liquid resin material is prevented from (1) creeping to above the structure and (ii) adhering to the plurality of linear electrically conductive members. The above method therefore makes it possible obtain an ion generating device which prevents a decrease in the ion generating capability of the discharge electrode.

In another aspect of the present invention, the ion generating device 1 of the preceding aspects can be arranged such that respective tip surfaces 36A and 37A of the two discharge electrodes 21A and 22A are each inclined downwards toward an opposing one of the two discharge electrodes 21A and 22A.

This configuration makes it possible for the tip surfaces to efficiently receive air blown between the two discharge electrodes. The configuration therefore makes it possible to release and spread ions more from the tip surfaces more efficiently.

In an ion generating device 2 in accordance with Aspect 8 of the present invention, the ion generating device of Aspects 1 to 5 is preferably arranged so as to further include a cleaning member (cleaning plates 55, cleaning plate 61) provided upwind of the discharge electrode 21•22 in the air sending direction A, the cleaning member (cleaning plates 55, cleaning plate 61) being configured to clean a discharge section (tip parts 31 and 32) of the discharge electrode 21•22 by being driving by air, sent in the air sending direction A, so as to come into contact with the discharge section (tip parts 31 and 32).

With the above configuration, the discharge section of the discharge electrode is cleaned by the cleaning member being driven by an external force due to air being sent. In other words, cleaning of the discharge section of the discharge electrode is carried out passively. As such, there is no need for a user to actively clean the discharge section of the discharge electrode, and cleaning of the discharge section is carried out passively (automatically). The cleaning of the discharge section of the discharge electrode is carried out upon commencement of sending air to the discharge electrode. This avoids a problem of the user forgetting the cleaning and thus makes it possible to reduce dirtying of the discharge section of the discharge electrode which dirtying is caused by the user forgetting the cleaning. It is therefore possible to reduce a decrease in the amount of ions generated.

An electrical apparatus 100 in accordance with another aspect of the present invention preferably includes: the above ion generating device 1; and an air sending device 103 configured to send a gas, in the air sending direction A, to the discharge electrodes 21 and 22. This configuration makes it possible to obtain an electronic apparatus which can release ions efficiently.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

REFERENCE SIGNS LIST

1 Ion generating device
10 Case
11 External connection substrate
12 Transformer drive circuit substrate
13 High voltage transformer
14 Ion generating element substrate
14a Long side
15 Lid
16 Connection terminal
21, 22, 22A Discharge electrode
21A to 21 Discharge electrode
23, 24 Induction electrode
25, 26, 26A Electrically conductive members
25A to 25C Electrically conductive members
31, 32, 32A Tip part
31A to 31C Tip part
33, 34 Base end part
33D to 33J Base end part
33a, 34a Mounting part
33Da to 33Ja Mounting part
33b, 34b Binding part
33Da1 to 33Ja 1 Extending part
33Da1a to 33Ja1a Base end part
33Da1b to 33Ja1b Connection end
33Da2 to 33Ha2 Structure
36, 37, 36A to 36C, 37A Tip surface
38 Base end surface
41 Insulating sealing member
51, 52, 53, 54 Protective plate
51a, 52a, 53a, 54a Opening
55, 61 Cleaning plate (cleaning member)
51 Protective plate
51, 52 Protective plate
51a Opening
51a, 52a Opening
52 Protective plate
52a Opening
53 Protective plate
53, 54 Protective plate
53a, 54a Opening
54b Upper end part
55 Cleaning plate 55a Upper end part
55b Airflow receiving surface
55c Counter surface
56 Rotation shaft
60 Spring
61 Cleaning plate
61a Upper end part
61b Airflow receiving surface
61c Counter surface
100 Electrical apparatus
101 Fan casing
102 Air flow path
103 Air sending device

The invention claimed is:

1. An ion generating device comprising:
a discharge electrode for generating ions by electric discharge,
the discharge electrode including (i) a tip part having a plurality of linear electrically conductive members, (ii) a binding part for binding together respective base end parts of the plurality of linear electrically conductive members, and (iii) a mounting part for mounting the binding part on the ion generating device,
the plurality of linear electrically conductive members forming a tip surface which is shaped so as to have a longer dimension direction and a shorter dimension direction,
an air sending direction, in which gas is sent to the discharge electrode in order to carry the ions, being nonparallel to the longer dimension direction of the tip surface,
wherein the tip surface has a plurality of ridge-shaped portions, each of the plurality of ridge-shaped portions comprising the plurality of linear electrically conductive members.

2. The ion generating device according to claim 1, wherein the longer dimension direction of the tip surface is perpendicular to the air sending direction.

3. The ion generating device according to claim 1, wherein:
the discharge electrode includes two discharge electrodes; and
a direction along which the two discharge electrodes are arranged is perpendicular to the air sending direction.

4. The ion generating device according to claim 1, further comprising a resin with which to seal a base end part of the mounting part,
the mounting part including (i) an extending part which extends from the base end part of the mounting part to a connection end of the mounting part at which connection end the mounting part connects to the binding part and (ii) a structure which is provided to the extending part and has a shape differing from that of the extending part.

5. The ion generating device according to claim 4, wherein the structure includes at least one of a protrusion from the extending part, a depression in the extending part, and an opening formed in the extending part.

6. A method for producing the ion generating device recited in claim 5, comprising the step of:
forming the resin by curing a liquid resin material.

7. The ion generating device according to claim 1, further comprising a cleaning member provided upwind of the discharge electrode in the air sending direction, the cleaning member being configured to clean a discharge section of the discharge electrode by being driving by air, sent in the air sending direction, so as to come into contact with the discharge section.

8. The ion generating device according to claim 1, wherein: the plurality of linear electrically conductive members of the tip part each have an outside diameter of not less than 5 μm and not more than 30 μm.

9. An ion generating device comprising:
a discharge electrode for generating ions by electric discharge,
the discharge electrode including (i) a tip part having a plurality of linear electrically conductive members, (ii) a binding part for binding together respective base end parts of the plurality of linear electrically conductive members, and (iii) a mounting part for mounting the binding part on the ion generating device,
the plurality of linear electrically conductive members forming a tip surface which is shaped so as to have a longer dimension direction and a shorter dimension direction,
an air sending direction, in which gas is sent to the discharge electrode in order to carry the ions, being nonparallel to the longer dimension direction of the tip surface, wherein:
the tip surface is formed by respective tip surfaces of the plurality of linear electrically conductive members which are bound together;
the ion generating device comprises two discharge electrodes; and
a tip surface of each of the two discharge electrodes is inclined downwards toward the other of the two discharge electrodes which is opposite the each of the two discharge electrodes.

10. An ion generating device comprising:
a discharge electrode for generating ions by electric discharge,
the discharge electrode including (i) a tip part having a plurality of linear electrically conductive members, (ii) a binding part for binding together respective base end parts of the plurality of linear electrically conductive members, and (iii) a mounting part for mounting the binding part on the ion generating device,
the plurality of linear electrically conductive members forming a tip surface which is shaped so as to have a longer dimension direction and a shorter dimension direction,
an air sending direction, in which gas is sent to the discharge electrode in order to carry the ions, being nonparallel to the longer dimension direction of the tip surface, wherein
the ion generating device further comprising a cleaning member provided upwind of the discharge electrode in the air sending direction, the cleaning member being configured to clean a discharge section of the discharge electrode by being driving by air, sent in the air sending direction, so as to come into contact with the discharge section.

* * * * *